US006974895B1

(12) United States Patent
Paiva et al.

(10) Patent No.: US 6,974,895 B1
(45) Date of Patent: Dec. 13, 2005

(54) TRANSGENIC LEGUME PLANTS MODIFIED TO PRODUCE RESVERATROL GLUCOSIDE AND USES THEREOF

(75) Inventors: Nancy L. Paiva, Ardmore, OK (US); John D. Hipskind, Durham, NC (US)

(73) Assignee: The Samuel Roberts Noble Foundation, Inc., Ardmore, OK (US)

( * ) Notice: Subject to any disclaimer, the term of this patent is extended or adjusted under 35 U.S.C. 154(b) by 0 days.

(21) Appl. No.: 09/890,167

(22) PCT Filed: Jan. 28, 2000

(86) PCT No.: PCT/US00/02366

§ 371 (c)(1),
(2), (4) Date: Jul. 27, 2001

(87) PCT Pub. No.: WO00/44921

PCT Pub. Date: Aug. 3, 2000

Related U.S. Application Data
(60) Provisional application No. 60/117,888, filed on Jan. 29, 1999.

(51) Int. Cl.[7] .............................. A01H 1/00; A01H 5/00; A01H 5/10; C12N 15/82; A23L 1/29
(52) U.S. Cl. ....................... 800/301; 426/615; 435/419; 800/279; 800/298; 800/312
(58) Field of Search ................................. 435/419, 415, 435/418; 800/279, 301, 312, 298; 426/615

(56) References Cited

U.S. PATENT DOCUMENTS

| | | | | |
|---|---|---|---|---|
| 5,106,739 A | * | 4/1992 | Comai et al. ................ | 800/294 |
| 5,689,046 A | * | 11/1997 | Schroder et al. ............ | 800/301 |
| 5,689,047 A | * | 11/1997 | Hain et al. ................... | 800/301 |

FOREIGN PATENT DOCUMENTS

| | | | | |
|---|---|---|---|---|
| EP | 0309862 | 4/1988 | ........... | C12N/15/00 |
| EP | 0773020 | 5/1997 | ......... | A61K/31/205 |
| GB | 2317561 | 4/1998 | .......... | A61K/35/78 |
| JP | 61171427 | 8/1986 | .......... | A61K/31/05 |

OTHER PUBLICATIONS

Fischer, Regina, Dec. 1994, Doctoral Dissertation, "Optimierung der heterlogen Expression von Stilbensynthasegenen fu den Pflanzenschutz", Institut fir Biotechnologie des Geschaftsbereichs Ptlanzenschutz der Bayer AG. Leverkusen.*

Kobayashi et al 2000, Plant Cell Reports vol. 19, pp. 904–910.*

Fischer, Regina, Dec. 1994, Doctoral Dissteration, "Optimierung der heterlogen Expression von Stilbensynthasegenen fu den Pflanzenschutz", Institut fiir Biotechnologie des Geschaftsbereichs Ptlanzenschutz der Bayer AG. Leverkusen. English translation of pp. 106–115. Sep. 2004.*

Fischer, Regina, Dec. 1994, Doctotal Dissertation, "Optimierung der heterlogen Expression von Stilbensynthasegenen fu den Pflanzenschutz", Institut fiir Biotechnologie des Geschaftsbereichs Ptlanzenschutz der Bayer AG. Leverkusen.*

Tropf et al 1994, J. Mol. Evol. 38:610–618.*

Leekband and Lorz, Theoretical and Applied Genetics Jun. 1998, 96:1004–1012.*

Alcubilla, M. 1970. "Extraction, chromatographic separation, and isolation of fungistatic substances from the inner bank of Norway spruce "Z. Pflanzeneraeher. Bodenk 127:64–74, abstract only.

Arichi, et al. 1982 "Effects of stilbene components of the roots of *Polygonum cuspidatum* Seib. et Zucc. on lipid metabolism," Chem *Pharm Bull* 30:1766–1770.

Bingham, et al. 1975. "Breeding alfalfa which regenerates from callus tissue in culture," *Crop. Sci* 15·719–721.

Bingham, et al. 1991. "Registration of alfalfa hybrid Regen–Sy germplasm for tissue culture and transformation research," *Crop Sci* 31:1098.

Dellaporta, et al. 1983. "A plant DNA minipreparation: version II," *Plant Mol Biol Rep* 1:19–21.

Dercks, et al. "Stibene phytoalexins and disease resistance in *Vitis*" 1995. In *Handbook of Phytoalexin Metabolism and Action*, M. Daniel and R.P. Purkayastha, eds, Marcel Dekker, Inc. USA, pp. 287–315.

Eckenrode, et al. 1985. "Comparison of the nucleotide sequence of soybean 18S rRNA with the sequences of other small–subunit rRNAs," *J Mol Evol* 21:259–269.

Fischer, et al. 1997. "Stilbene synthase gene expression causes changes in flower colour and male sterility in tobacco," *Plant Journal* 11(3):489–498.

Fitzpatrick, et al. 1993. "Endothelium–dependent vasorelacing activity of wine and other grape products," *Am. J. Physiol* 265:H774–H778.

Goldberg, et al. 1996. "Resveratrol glucosides are important components of commercial wines," *Am J. Enology and Viticulture* 47(4):415–420 (abstract only).

Hain, et al. 1990. "Expression of a stilbene synthase gne in *Nicotiana tobacum* results in synthesis of the phytoalexin resveratrol," *Plant Mol Biol* 15:325–335.

Hain et al. 1993. "Disease resistance results from forgien phytoalexin expression in a novel plant," *Nature* 361:153–156.

(Continued)

*Primary Examiner*—David H Kruse
(74) *Attorney, Agent, or Firm*—Fulbright & Jaworski L.L.P.

(57) ABSTRACT

The invention relates to producing resveratrol glucoside in edible legume plants by transforming with a transgene encoding resveratrol synthase operably linked to a constitutive promoter. The invention relates to products containing and methods of using transformed edible legume plants and edible material of the transformed legume plants as a foodstuff, a nutritional supplement, an animal feed supplement or a nutraceutical. The invention further relates to a method of increasing disease resistance in an edible legume plant by transforming with a transgene encoding resveratrol synthase operably linked to a constitutive promoter.

32 Claims, 19 Drawing Sheets

OTHER PUBLICATIONS

Hillis, et al. 1974. "Polyphenols of *Eucalyptus sideroxylon* wood," *Phytochemistry* 13:1591–1595.

Ingham, J.L. 1976. 3,5,4'–Trihydroxystilbene as a phytoalexin from groundnuts (*Arachis hypogaea*). *Phytochemistry* 15, 1791–1793.

Jang, et al. 1997. "Cancer chemopreventive activity of resveratrol, a natural product derived from grapes," *Science* 275:218–220.

Jayatilake, et al. 1993. "Kinase inhibitors from *Polygonum cuspidatum*," *J. Natural Products* 56(10):1805–1810.

Jeandet, et al. 1994. "Occurrence of a resveratrol-β-D-glucoside in wine: preliminary studies," *Vitits* 33:183–184.

Junghans, et al. 1993. "Stress response in alfalfa (*Medicago sativa* L.) 15. Characterization and expression patterns of members of a subset of the chalcone synthase multigene family," *Plant Mol Biol* 22:239–253.

Keogh, et al. 1980. "Comparison of histological and physiological responses to *Phykospora pachyrhizi* in resistant and susceptible soybeans," *Trans Br Mycol Soc* 74:329–333.

Kimura, et al. 1983. "Effects of stilbene components of roots of Polygonum ssp. on liver injury in peroxidized oil–fed rats," *Plant Med J Med Plant Res* 49:51–54.

Kimura, et al. 1985. "Effects of stilbenes on arachidonate metabolism in leukocytes," *Biochem Biophys Acta* 834:275–278.

Langcake, P. and Prcye, R.J. 1976. "The production of resveratrol by *Vitis vinifera* and other members of the Vitaceae as a response to infection or injury," *Physiol Plant Pathol* 9:77–86.

Leath, K.T., "Spring black stem and leaf spot." In *Compendium of Alfalfa Diseases*, D.L. Stuteville & D.C. Erwin, 2$^{nd}$ ed., American Phytopathological Society Press, 1990, p. 16–17.

Leckband, et al. 1998. "Transformation and expression of a stilbene synthase gene of *Vitis vinifera* L. in barley and wheat for increased fungal resistance," *Theoretical and Applied Genetics* 96(8):1004–1012.

Logemann, et al. 1987. "Improved method for isolation of RNA from plant tissues," *Anal Biochem* 163:16–20.

Mattivi, et al. 1995. "Isolation, characterization, and evolution in red wine vinification of resveratrol monomers," *J Argri Food Chem* 43:1820–1823.

Murashige, T. and Skoog, F. 1962. "A revised media for rapid growth and bio assays with tobacco tissue culture," *Physiol Plant* 15:473–497.

Olivo, S. and Wargovich, M.J. 1998. "Inhibition of aberant crypt foci by chemopreventive agents," *In–Vivo* 12:159–166.

Oommen, et al. 1994. "The elicitor–inducible alfalfa isoflavone reductase promoter different patterns of developmental expression in homologous and heterlogous transgenic plants," *Plant Cell* 6:1789–1803.

Orsini, et al. 1997. "Isolation, synthesis, and antiplatelet aggregation activity of resveratrol 3–O–beta–D–glucopyramoside and related compounds," *J. Natural Products* 60(11):1082–1087.

Powell, et al. 1994. "Isolation of resveratrol from *Festuca versuta* and evidence of the widespread occurrence of this stilbene in the *Poaceae*," *Phytochemistry* 35:335–338.

Restrepo, et al. 1990. "Nuclear transport of plant polyviral proteins," *Plant Cell* 2:987–998.

Soleas, et al. 1997. "Resveratrol: a molecule whose time has come? And gone?" *Clinical Biochemistry* 30(2):91–113.

Soleas, et al. 1997. "Wine as a biological fluid: history, production, and role in disease prevention," *J Clin Lab Anal* 11: 287–313.

Sotheeswaran, S. and Pasupathy, V. 1993. "Distribution of resveratrol oligomers in plants," *Phytochemistry* 32:1083–1092.

Stark–Lorenzen, et al. 1997. "Transfer of a grapevine stilbene synthase gene to rice (*Oryza Sativa* L.)," *Plant Cell Rep* 16:668–673.

Steele, et al. 1998. "Cancer chemoprevention drug development strategies for resveratrol," *Pharm Bio* 36:62–68 suppl.

Teguo, et al. 1998. "Isolation, identification, and antioxidant activity of three stilbene glucosides newly extracted from *Vitis vinifera* cell cultures," *J Nat Prod* 61:655–657.

Thomzik, et al. 1997. "Synthesis of a grapevine photoalexin in transgenic tomatoes (Lycopersicon esculentum Mill.) conditions resistance against Phytophthora infestans," *Physiological and Molecular Plant Pathology* 51(4):265–278 (abstract only).

Tropf. et al. 1994. "Evidence that stilbene synthases have developed from chalcone synthases several times in the course of evolution," *J Mol Evol* 38:610–618.

Wang, et al. 1995. "Reducing effect of 3, 4', 5–trihydroxystibene–3–β–mono–D–gluocside on arterial thrombosis induced by vascular endothelial injury," *Acta Pharmacologica Sinica* 16(2):159–162.

Waterhouse, et al. 1994. "The occurrence of piceid, a stilbene glucoside, in grape berries," *Phytochemistry* 37(2):571–573 (abstract only).

Zhang, et al. 1995. "Influence of 3,4', 5–trihydroxystibene–3–β–mono–D–gluocside on vascular endothelial epoprostenol and platelet aggregation," *Acta Pharmacologica Sinica* 16(3):265–268.

Zhou, J. and Goldsbrough, P.B. 1993. "An Arabidopis gene with homology to glutathione S–transferase is regulated by ethylene," *Plant Mol Biol* 22:517–523.

* cited by examiner

| | | | | | |
|---|---|---|---|---|---|
| AAGCTTGCAT | GCCTGCAGGT | CAACATGGTG | GAGCACGACA | CACTTGTCTA | CTCCAAAAAT | 60
| ATCAAAGATA | CAGTCTCAGA | AGACCAAAGG | GCAATTGAGA | CTTTTCAACA | AAGGGTAATA | 120
| TCCGGAAACC | TCCTCGGATT | CCATTGCCCA | GCTATCTGTC | ACTTTATTGT | GAAGATAGTG | 180
| GAAAAGGAAG | GTGGCTCCTA | CAAATGCCAT | CATTGCGATA | AAGGAAAGGC | CATCGTTGAA | 240
| GATGCCTCTG | CCGACAGTGG | TCCCAAAGAT | GGACCCCCAC | CCACGAGGAG | CATCGTGGAA | 300
| AAAGAAGACG | TTCCAACCAC | GTCTTCAAAG | CAAGTGGATT | GATGTGTCAA | CATGGTGGAG | 360
| CACGACACAC | TTGTCTACTC | CAAAAATATC | AAAGATACAG | TCTCAGAAGA | CCAAAGGGCA | 420
| ATTGAGACTT | TTCAACAAAG | GGTAATATCC | GGAAACCTCC | TCGGATTCCA | TTGCCCAGCT | 480
| ATCTGTCACT | TTATTGTGAA | GATAGTGGAA | AAGGAAGGTG | GCTCCTACAA | ATGCCATCAT | 540
| TGCGATAAAG | GAAAGGCCAT | CGTTGAAGAT | GCCTCTGCCG | ACAGTGGTCC | CAAAGATGGA | 600
| CCCCCACCCA | CGAGGAGCAT | CGTGGAAAAA | GAAGACGTTC | CAACCACGTC | TTCAAAGCAA | 660
| GTGGATTGAT | GTGATATCTC | CACTGACGTA | AGGGATGACG | CACAATCCCA | CTATCCTTGC | 720
| AAGACCCTTC | CTCTATATAA | GGAAGTTCAT | TTGGAGAGGA | CCTCGAGAAT | TCTCAACACA | 780
| ACATATACAA | AACAAACGAA | TCTCAAGCAA | TCAAGCATTC | TACTTCTATT | GCAGCAATTT | 840
| AAATCATTTC | TTTTAAAGCA | AAAGCAATTT | TCTGAAAATT | TTCACCATTT | ACGAACGATA | 900
| GCCATGGAAG | GGGGAATTCG | CAAGGTTCAA | AGGGCAGAAG | GTCCAGCAAC | TGTATTGGCA | 960
| ↑↑↑↑↑↑ | | | | | |
| ATTGGAACAG | CAAATCCACC | GAACTGTATT | GATCAGAGTA | CATATGCAGA | TTATTATTTT | 1020
| AGAGTAACCA | ATAGCGAACA | CATGACTGAT | CTCAAGAAGA | AATTTCAGCG | CATCTGTGAG | 1080
| AGAACACAGA | TCAAGAACAG | ACATATGTAC | TTAACAGAAG | AGATACTAAA | AGAAAATCCT | 1140
| AACATGTGTG | CATACAAGGC | ACCGTCATTG | GATGCAAGAG | AAGACATGAT | GATCAGGGAG | 1200
| GTACCAAGAG | TTGGAAAAGA | GGCTGCAACC | AAGGCCATCA | AGGAATGGGG | CCAGCCAATG | 1260
| TCTAAGATCA | CACATTTGAT | CTTCTGCACC | ACCAGCGGCG | TTGCGTTGCC | TGGCGTTGAT | 1320
| TACGAACTCA | TCGTACTTTT | AGGGCTGGAC | CCATGCGTCA | AGAGGTACAT | GATGTACCAC | 1380
| CAAGGTTGCT | TCGCTGGTGG | CACTGTCCTT | CGTTTGGCTA | AGGACTTGGC | TGAAAACAAC | 1440
| AAGGATGCTC | GTGTACTTAT | CGTTTGTTCT | GAGAATACCG | CAGTCACTTT | CCGCGGTCCT | 1500
| AGTGAGACAG | ACATGGATAG | TCTTGTAGGA | CAAGCATTGT | TTGCCGATGG | AGCTGCTGCG | 1560
| ATTATCATTG | GTTCTGATCC | TGTGCCAGAG | GTTGAGAAGC | CTATCTTTGA | GCTTGTTTCG | 1620
| ACCGATCAAA | AACTTGTCCC | TGGCAGCCAT | GGAGCCATCG | GTGGTCTCCT | TCGTGAAGTT | 1680
| GGACTTACAT | TCTATCTTAA | CAAGAGTGTT | CCTGATATTA | TTTCGCAAAA | TATCAATGAC | 1740
| CCGCTCAATA | AAGCTTTTGA | TCCATTGGGT | ATTTCTGATT | ATAACTCAAT | ATTTTGGATT | 1800
| GCACATCCTG | GTGGGCGTGC | AATTTTGGAC | CAGGTTGAAC | AGAAGGTGAA | CTTGAAGCCA | 1860
| GAGAAGATGA | AAGCCACTAG | AGATGTGCTT | AGCAATTATG | GTAACATGTC | AAGTGCCTGT | 1920

FIG. 1A

```
GTGTTCTTCA TTATGGATTT GATGAGGAAG AGGTCTCTTG AAGAAGGACT TAAAACTACC    1980
GGAGAAGGAC TTGATTGGGG TGTGCTTTTT GGCTTTGGTC CTGGTCTCAC TATTGAAACT    2040
GTCGTTCTCC GCAGTGTGGC CATATAATGC ACTTAATTAT GCATATATGC GATTGTGTTA    2100
TTTTTTAATA ATTTTCTTTG GCTCTAAAAT AAGCTAAGGT GCTGAATGGC TCATATATTA    2160
TTAGATGAGT GAAAAATTAA AAAAAGATGT CCAAAGTTAA TTCTTTATGC AAACATCATT    2220
CAATATCAAA GTCTGTAATT GTTAGTAAAA AATTATATCA AATTCTTTTC AATCGAGCAG    2280
CATAACACAT GCCTTTATTG ATTGGGTTGT AATTTAAGTC TGATTGCACT GTGCACAACA    2340
TTTCAAAAGT ATATGTCTCC TATTCTCAAT CATATGAAAC CGTTTGAGTA CACAGCATTT    2400
TTTGATAGGG TTGGTGATTT TGATTTGTTA GATTAGTTTG TTAGGGTTTG GTTTTTTATT    2460
TTTAGGGAAT TTTTATTCTA ATTTAAATAT ACTGATTTTT AGGGATTTTT GTATCTTAAA    2520
TATATGAGAG AAAAAAGTGA GACGTTAATT TCTAAAAAAA CGAGGTGCTA ATTTGGTTCG    2580
AACAAAACTT TGGAGAATCA ATTTGAATTA CATATGTGAA GTTTGATAAA TTATTTTGGC    2640
TATTTACTCA TAAAAAGTTA TTAAATGTGT AGTTGTATTT AACATTTTTT TTATTAACAA    2700
CGGGGTTTAA TGGTAAAAGA AAAATAAACT AAAAGACAAT ACTTGAAAAT GAGATACCGA    2760
TAAAATCAGC ATGAAGACGA AGAGAAGTAC AAAAGGATAA ATTAATGAAT TTACATTATT    2820
CATACTAAGG TAATATATTT ATTGATGGGG ATCCTCTAGA GTCCGCAAAA ATCACCAGTC    2880
                                 .......
TCTCTCTACA AATCTATCTC TCTCTATTTT TCTCCAGAAT AATGTGTGAG TAGTTCCCAG    2940
ATAAGGGAAT TAGGGTTCTT ATAGGGTTTC GCTCATGTGT TGACCATATA AGAAACCCTT    3000
AGTATGTATT TGTATTTGTA AAATACTTCT ATCAATAAAA TTTCTAATTC CTAAAACCAA    3060
AATCCAGTGA CCTGCAGGCA TGCAAGCTT                                     3089
              *****
```

FIG. 1B

SEQUENCE LISTING

<160> NUMBER OF SEQ ID NOS: 4

<210> SEQ ID NO 1
<211> LENGTH: 3089
<212> TYPE: DNA
<213> ORGANISM: Arachis hypogaea
<220> FEATURE:
<221> NAME/KEY: CDS
<222> LOCATION: (904)..(2064)

<400> SEQUENCE: 1

```
aagcttgcat gcctgcaggt caacatggtg gagcacgaca cacttgtcta ctccaaaaat      60
atcaaagata cagtctcaga agaccaaagg gcaattgaga cttttcaaca aagggtaata     120
tccggaaacc tcctcggatt ccattgccca gctatctgtc actttattgt gaagatagtg     180 gaaaggaag gtggctccta caaatgccat cattgcgata aggaaaggc catcgttgaa       240 gatgcctctg ccgacagtgg tcccaaagat ggaccccac ccacgaggag catcgtggaa      300
aaagaagacg ttccaaccac gtcttcaaag caagtggatt gatgtgtcaa catggtggag     360
cacgacacac ttgtctactc caaaaatatc aaagatacag tctcagaaga ccaaagggca     420
attgagactt tcaacaaag ggtaatatcc ggaaacctcc tcggattcca ttgcccagct      480
atctgtcact ttattgtgaa gatagtggaa aaggaaggtg gctcctacaa atgccatcat    540
tgcgataaag gaaaggccat cgttgaagat gcctctgccg acagtggtcc caaagatgga    600
cccccaccca cgaggagcat cgtggaaaaa gaagacgttc caaccacgtc ttcaaagcaa    660
gtggattgat gtgatatctc cactgacgta agggatgacg cacaatccca ctatccttgc    720
aagacccttc ctctatataa ggaagttcat ttggagagga cctcgagaat tctcaacaca    780
acatatacaa aacaaacgaa tctcaagcaa tcaagcattc tacttctatt gcagcaattt    840
aaatcatttc ttttaaagca aaagcaattt tctgaaaatt ttcaccattt acgaacgata    900 gcc atg gaa ggg gga att cgc aag gtt caa agg gca gaa ggt cca gca      948
    Met Glu Gly Gly Ile Arg Lys Val Gln Arg Ala Glu Gly Pro Ala
      1               5                  10                  15 act gta ttg gca att gga aca gca aat cca ccg aac tgt att gat cag      996
Thr Val Leu Ala Ile Gly Thr Ala Asn Pro Pro Asn Cys Ile Asp Gln
             20                  25                  30
```

```
                                                      -continued agt aca tat gca gat tat tat ttt aga gta acc aat agc gaa cac atg        1044
Ser Thr Tyr Ala Asp Tyr Tyr Phe Arg Val Thr Asn Ser Glu His Met
             35                  40                  45 act gat ctc aag aag aaa ttt cag cgc atc tgt gag aga aca cag atc        1092
Thr Asp Leu Lys Lys Lys Phe Gln Arg Ile Cys Glu Arg Thr Gln Ile
         50                  55                  60 aag aac aga cat atg tac tta aca gaa gag ata cta aaa gaa aat cct        1140
Lys Asn Arg His Met Tyr Leu Thr Glu Glu Ile Leu Lys Glu Asn Pro
 65                  70                  75 aac atg tgt gca tac aag gca ccg tca ttg gat gca aga gaa gac atg        1188
Asn Met Cys Ala Tyr Lys Ala Pro Ser Leu Asp Ala Arg Glu Asp Met
 80                  85                  90                  95 atg atc agg gag gta cca aga gtt gga aaa gag gct gca acc aag gcc        1236
Met Ile Arg Glu Val Pro Arg Val Gly Lys Glu Ala Ala Thr Lys Ala
                 100                 105                 110 atc aag gaa tgg ggc cag cca atg tct aag atc aca cat ttg atc ttc        1284
Ile Lys Glu Trp Gly Gln Pro Met Ser Lys Ile Thr His Leu Ile Phe
             115                 120                 125 tgc acc acc agc ggc gtt gcg ttg cct ggc gtt gat tac gaa ctc atc        1332
Cys Thr Thr Ser Gly Val Ala Leu Pro Gly Val Asp Tyr Glu Leu Ile
         130                 135                 140 gta ctt tta ggg ctg gac cca tgc gtc aag agg tac atg atg tac cac        1380
Val Leu Leu Gly Leu Asp Pro Cys Val Lys Arg Tyr Met Met Tyr His
 145                 150                 155 caa ggt tgc ttc gct ggt ggc act gtc ctt cgt ttg gct aag gac ttg        1428
Gln Gly Cys Phe Ala Gly Gly Thr Val Leu Arg Leu Ala Lys Asp Leu
 160                 165                 170                 175 gct gaa aac aac aag gat gct cgt gta ctt atc gtt tgt tct gag aat        1476
Ala Glu Asn Asn Lys Asp Ala Arg Val Leu Ile Val Cys Ser Glu Asn
                 180                 185                 190 acc gca gtc act ttc cgc ggt cct agt gag aca gac atg gat agt ctt        1524
Thr Ala Val Thr Phe Arg Gly Pro Ser Glu Thr Asp Met Asp Ser Leu
             195                 200                 205 gta gga caa gca ttg ttt gcc gat gga gct gct gcg att atc att ggt        1572
Val Gly Gln Ala Leu Phe Ala Asp Gly Ala Ala Ala Ile Ile Ile Gly
         210                 215                 220 tct gat cct gtg cca gag gtt gag aag cct atc ttt gag ctt gtt tcg        1620
Ser Asp Pro Val Pro Glu Val Glu Lys Pro Ile Phe Glu Leu Val Ser
 225                 230                 235 acc gat caa aaa ctt gtc cct ggc agc cat gga gcc atc ggt ggt ctc        1668
Thr Asp Gln Lys Leu Val Pro Gly Ser His Gly Ala Ile Gly Gly Leu
 240                 245                 250                 255 ctt cgt gaa gtt gga ctt aca ttc tat ctt aac aag agt gtt cct gat        1716
Leu Arg Glu Val Gly Leu Thr Phe Tyr Leu Asn Lys Ser Val Pro Asp
                 260                 265                 270 att att tcg caa aat atc aat gac gcg ctc aat aaa gct ttt gat cca        1764
Ile Ile Ser Gln Asn Ile Asn Asp Ala Leu Asn Lys Ala Phe Asp Pro
             275                 280                 285 ttg ggt att tct gat tat aac tca ata ttt tgg att gca cat cct ggt        1812
Leu Gly Ile Ser Asp Tyr Asn Ser Ile Phe Trp Ile Ala His Pro Gly
         290                 295                 300 ggg cgt gca att ttg gac cag gtt gaa cag aag gtg aac ttg aag cca        1860
Gly Arg Ala Ile Leu Asp Gln Val Glu Gln Lys Val Asn Leu Lys Pro
 305                 310                 315 gag aag atg aaa gcc act aga gat gtg ctt agc aat tat ggt aac atg        1908
Glu Lys Met Lys Ala Thr Arg Asp Val Leu Ser Asn Tyr Gly Asn Met
 320                 325                 330                 335 tca agt gcc tgt gtg ttc ttc att atg gat ttg atg agg aag agg tct        1956
Ser Ser Ala Cys Val Phe Phe Ile Met Asp Leu Met Arg Lys Arg Ser
                 340                 345                 350
```

```
ctt gaa gaa gga ctt aaa act acc gga gaa gga ctt gat tgg ggt gtg    2004
Leu Glu Glu Gly Leu Lys Thr Thr Gly Glu Gly Leu Asp Trp Gly Val
            355                 360                 365 ctt ttt ggc ttt ggt cct ggt ctc act att gaa act gtc gtt ctc cgc    2052
Leu Phe Gly Phe Gly Pro Gly Leu Thr Ile Glu Thr Val Val Leu Arg
    370                 375                 380 agt gtg gcc ata taatgcactt aattatgcat atatgcgatt gtgttatttt        2104
Ser Val Ala Ile
        385 ttaataattt tctttggctc taaaataagc taaggtgctg aatggctcat atattattag  2164
atgagtgaaa aattaaaaaa agatgtccaa agttaattct ttatgcaaac atcattcaat  2224
atcaaagtct gtaattgtta gtaaaaaatt atatcaaatt cttttcaatc gagcagcata  2284
acacatgcct ttattgattg ggttgtaatt taagtctgat tgcactgtgc acaacatttc  2344
aaaagtatat gtctcctatt ctcaatcata tgaaaccgtt tgagtacaca gcatttttg   2404
ataggttgg tgattttgat tgttagatt agtttgttag ggtttggttt tttatttta    2464
gggaattttt attctaattt aaatatactg attttagg atttttgtat cttaaatata    2524
tgagagaaaa aagtgagacg ttaatttcta aaaaacgag gtgctaattt ggttcgaaca   2584
aaactttgga gaatcaattt gaattacata tgtgaagttt gataaattat tttggctatt  2644
tactcataaa aagttattaa atgtgtagtt gtatttaaca ttttttttat taacaacggg  2704
gtttaatggt aaaagaaaaa taaactaaaa gacaatactt gaaatgaga taccgataaa   2764
atcagcatga agacgaagag aagtacaaaa ggataaatta atgaatttac attattcata  2824
ctaaggtaat atatttattg atggggatcc tctagagtcc gcaaaaatca ccagtctctc  2884
tctacaaatc tatctctctc tatttttctc cagaataatg tgtgagtagt tcccagataa  2944
gggaattagg gttcttatag ggtttcgctc atgtgttgag catataagaa acccttagta  3004
tgtatttgta tttgtaaaat acttctatca ataaaatttc taattcctaa aaccaaaatc  3064
cagtgacctg caggcatgca agctt                                        3089
```

<210> SEQ ID NO 2
<211> LENGTH: 387
<212> TYPE: PRT
<213> ORGANISM: Arachis hypogaea

<400> SEQUENCE: 2

```
Met Glu Gly Gly Ile Arg Lys Val Gln Arg Ala Glu Gly Pro Ala Thr
 1               5                  10                  15

Val Leu Ala Ile Gly Thr Ala Asn Pro Pro Asn Cys Ile Asp Gln Ser
            20                  25                  30

Thr Tyr Ala Asp Tyr Tyr Phe Arg Val Thr Asn Ser Glu His Met Thr
        35                  40                  45

Asp Leu Lys Lys Lys Phe Gln Arg Ile Cys Glu Arg Thr Gln Ile Lys
    50                  55                  60

Asn Arg His Met Tyr Leu Thr Glu Glu Ile Leu Lys Glu Asn Pro Asn
 65                 70                  75                  80

Met Cys Ala Tyr Lys Ala Pro Ser Leu Asp Ala Arg Glu Asp Met Met
                85                  90                  95

Ile Arg Glu Val Pro Arg Val Gly Lys Glu Ala Ala Thr Lys Ala Ile
           100                 105                 110

Lys Glu Trp Gly Gln Pro Met Ser Lys Ile Thr His Leu Ile Phe Cys
       115                 120                 125
```

```
Thr Thr Ser Gly Val Ala Leu Pro Gly Val Asp Tyr Glu Leu Ile Val
    130                 135                 140

Leu Leu Gly Leu Asp Pro Cys Val Lys Arg Tyr Met Met Tyr His Gln
145                 150                 155                 160

Gly Cys Phe Ala Gly Gly Thr Val Leu Arg Leu Ala Lys Asp Leu Ala
                165                 170                 175

Glu Asn Asn Lys Asp Ala Arg Val Leu Ile Val Cys Ser Glu Asn Thr
            180                 185                 190

Ala Val Thr Phe Arg Gly Pro Ser Glu Thr Asp Met Asp Ser Leu Val
            195                 200                 205

Gly Gln Ala Leu Phe Ala Asp Gly Ala Ala Ile Ile Ile Gly Ser
    210                 215                 220

Asp Pro Val Pro Glu Val Glu Lys Pro Ile Phe Glu Leu Val Ser Thr
225                 230                 235                 240

Asp Gln Lys Leu Val Pro Gly Ser His Gly Ala Ile Gly Gly Leu Leu
                245                 250                 255

Arg Glu Val Gly Leu Thr Phe Tyr Leu Asn Lys Ser Val Pro Asp Ile
            260                 265                 270

Ile Ser Gln Asn Ile Asn Asp Ala Leu Asn Lys Ala Phe Asp Pro Leu
            275                 280                 285

Gly Ile Ser Asp Tyr Asn Ser Ile Phe Trp Ile Ala His Pro Gly Gly
    290                 295                 300

Arg Ala Ile Leu Asp Gln Val Glu Gln Lys Val Asn Leu Lys Pro Glu
305                 310                 315                 320

Lys Met Lys Ala Thr Arg Asp Val Leu Ser Asn Tyr Gly Asn Met Ser
                325                 330                 335

Ser Ala Cys Val Phe Phe Ile Met Asp Leu Met Arg Lys Arg Ser Leu
            340                 345                 350

Glu Glu Gly Leu Lys Thr Thr Gly Glu Gly Leu Asp Trp Gly Val Leu
            355                 360                 365

Phe Gly Phe Gly Pro Gly Leu Thr Ile Glu Thr Val Val Leu Arg Ser
    370                 375                 380

Val Ala Ile
385

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: PCR primer
<221> NAME/KEY: misc_feature
<222> LOCATION: (1)..(20)

<400> SEQUENCE: 3
ccatggaagg gggaattcgc                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:  PCR primer
<221> NAME/KEY: misc_feature
<222> LOCATION: (1)..(20)
<223> OTHER INFORMATION: RS cDNA specific primer for PCR
```

```
<400> SEQUENCE: 4
gagccattca gcaccttagc                                                      20
```

TRANSGENIC LEGUME PLANTS MODIFIED TO PRODUCE RESVERATROL GLUCOSIDE AND USES THEREOF

CROSS-REFERENCE OF RELATED APPLICATION

This application is a National Phase Application under 35 U.S.C. §371 of International Application No. PCT/US00/02366 filed Jan. 28, 2000, which claims priority to U.S. Provisional Application No. 60/117,888 filed Jan. 29, 1999.

TECHNICAL FIELD OF INVENTION

This invention relates to transgenic plants and plant cells modified to accumulate resveratrol glucoside or to contain increased levels thereof.

BACKGROUND OF THE INVENTION

Stilbenes are biologically active phenolic compounds exhibiting a broad spectrum of antibiotic and pharmacological activities, and plants modified with respect to stilbene content may useful for various purposes. Diverse plants and plant families naturally produce stilbenes, including grape (Vitaceae), Scots pine (Cyperaceae), tall fescue (Poaceae), and peanut (Arachaceae) (Sotheeswaran, S. and Pasupathy, V. 1993. "Distribution of resveratrol oligomers in plants," *Phytochemistry* 32:1083–1092; Powell, et al. 1994. "Isolation of resveratrol from *Festuca versuta* and evidence of the widespread occurrence of this stilbene in the Poaceae," *Phytochemisty* 35:335–338; Ingram, J. L. 1976. "3,5,4'-Trihydroxystilbene as a phytoalexin from groundnut (*Arachis hypogaea*). *Phytochemistry* 15,1791–1793).

Stilbenes have been reported to play a role in plant resistance to fungal pathogens. Constitutive stilbene accumulation is believed to function as a mechanism of general resistance to microbial pathogens, while in some plants, stilbenes accumulate as phytoalexins in response to microbial attack.

Further, stilbenes are thought to have health-promoting effects, and plants containing stilbenes may be desirable in human and animal diets. Stilbenes have been shown to have a number of beneficial effects on human health, based on epidemiological studies and laboratory studies involving humans, animals, cell cultures and enzyme assays (Jang, et al. 1997. "Cancer chemopreventative activity of resveratrol, a natural product derived from grapes," *Science* 275:218–220).

Of particular interest is the stilbene resveratrol. Resveratrol is present in wine and may be involved in the health-promotive effects of moderate wine consumption. The increased consumption of resveratrol has been proposed as a way to reduce cancer rates and coronary heart disease in humans (Soleas, et al. 1997. "Wine as a biological fluid: history, production, and role in disease prevention," *J Clin Lab Anal* 11: 287–313). Resveratrol and plant extracts containing resveratrol have been shown to be effective in prevention and therapy of atherosclerosis (Arichi, et al. 1982. *Chem Pharm Bull* 30:1766), as an anti-inflammatory agent (Kimura, et al. 1985. *Biochem Biophys Acta* 834:275), and as an anti-hyperoxidative agent (Kimura, et al. 1983. *Plant Med J Med Plant Res* 49:51). Resveratrol showed significant inhibition of aberrant colon crypt formation in a carcinogen (azoxymethane) treated rat model, suggesting utility in inhibiting tumorogenesis in humans (Steele, et al. 1998. "Cancer chemoprevention drug development strategies for resveratrol," *Pharm Bio* 36:62–68 suppl). Resveratrol has also been found to promote the formation of nitroxides which are effective as vasodilatory agents and in inhibiting platelet aggregation (Fitzpatrick, et al. 1993. *Am J Physiol* 34:774).

Resveratrol has the following chemical structure:

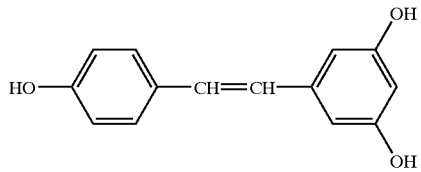

The biosynthetic pathway of resveratrol in plants involves stilbene synthase. Resveratrol is formed when stilbene synthase converts one molecule of p-coumaroyl-CoA and three molecules of malonyl-CoA into resveratrol, i.e., 3,5,4'-trihydroxystilbene. In some plant species, resveratrol production is inducible, and resveratrol accumulates as a phytoalexin following microbial attack (Langcake, P. and Pryce, R. J. 1976. "The production of resveratrol by *Vitis vinifera* and other members of the Vitaceae as a response to infection or injury," *Physiol Plant Pathol* 9:77–86; Dercks, et al. 1995. "Stilbene phytoalexins and disease resistance in *Vitis*." In *Handbook of Phytoalexin Metabolism and Action*, M. Daniel and R. P. Purkayastha, eds, Marcel Dekker, Inc. USA, pp. 287–315).

Not all plants naturally accumulate resveratrol or other stilbenes. Heterologous accumulation of resveratrol has been achieved in plants which do not naturally accumulate resveratrol by genetic engineering to express resveratrol synthase. For example, transformation of tobacco with a resveratrol synthase (RS) genomic clone from peanut resulted in the rapid accumulation of resveratrol following treatment of cell suspension cultures with fungal elicitor (Hain, et al. 1990. "Expression of a stilbene synthase gene in *Nicotiana tobacum* results in synthesis of the phytoalexin resveratrol," *Plant Mol Biol* 15:325–335). Subsequent experiments with an RS gene (Vst1) from *V. vinifera* L. demonstrated a significant level of resistance in transgenic tobacco, tomato, and rice to fungal pathogens *Botrytis cinerea, Phytophtora infestans,* and *Pyricularia oryzae,* respectively [Hain et al. 1993. "Disease resistance results from foreign phytoalexin expression in a novel plant," *Nature* 361:153–156; Thomzik, et al. 1997. "Synthesis of a grapevine phytoalexin in transgenic tomatoes (*Lycopersican esculetum* Mill.) conditions resistance against *Phytophthora infestans,*" *Physiol Mol Plant Path* 51:265–278; Stark-Lorenzen, et al. 1997. "Transfer of a grapevine stilbene synthase gene to rice (*Oryza sativa* L.)," *Plant Cell Rep* 16:668–673]. These reports demonstrated that accumulation of resveratrol in foreign plant species transformed with a resveratrol synthase gene provides a means by which a broad spectrum of increased resistance to fungal pathogens can be achieved in any plant. Increased resistance to fungal pathogens, in turn, results in increased crop production and reduction in the use of crop protection chemicals.

Accumulation of resveratrol has also been reported to have some negative side effects in plants. For example, Fischer, et al. reported that plants accumulating increased levels of resveratrol were rendered male sterile. Not only was the pollen destroyed, but the plants also demonstrated lower seed yields and altered flower color (Fischer, et al. 1997. "Stilbene synthase gene expression causes changes in flower colour and male sterility in tobacco, " *Plant J* 11:489–498).

Resveratrol-3-O-β-D-glucopyranoside (3,4',5-trihydroxystilbene-3-β-D-glucoside, polydatin, piceid; hereinafter referred to as "resveratrol glucoside" or "RGluc") is a resveratrol conjugate. The chemical structure for the trans and cis isomers are given below.

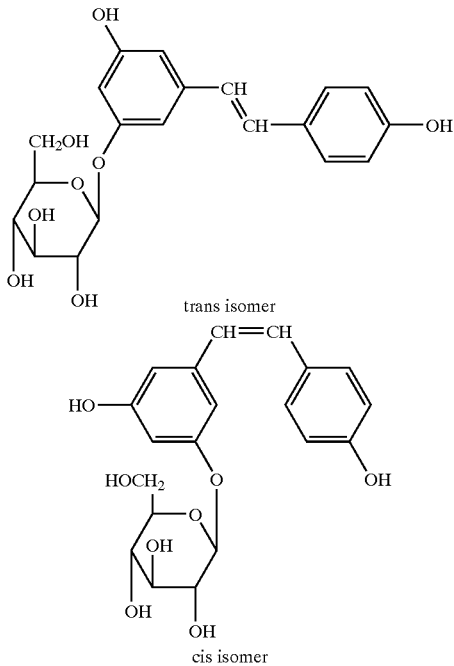

trans isomer cis isomer

Both trans- and cis-RGluc have been isolated from non-transgenic plants, for example, grapes (Jeandet, et al. 1994. "Occurrence of a resveratrol-β-D-glucoside in wine: preliminary studies," *Vitis* 33:183–184), *Eucalyptus sideroxylon* wood (Hillis, et al. 1974. "Polyphenols of *Eucalyptus sideroxylon* wood," *Phytochemistry* 13:1591–1595), and Norway spruce (Alcubilla-Marin, M. 1970. "Extraction, chromatographic separation, and isolation of fungistatic substances from the inner bark of Norway spruce," *Z. Pflanzenernaehr. Bodenk.* 127:64–74).

It has been reported that human benefits previously thought to be due to resveratrol are also attributable to RGluc. For example, in International Application WO 9958119, a method for preventing or treating restenosis, a medical condition characterized by recurrent stricture of a heart valve, and for preventing the recurrence or progression of coronary heart disease was provided which involves administration of an active agent comprising cis-resveratrol, trans-resveratrol a mixture thereof, or a pharmacologically acceptable salt, ester, amide, prodrug, or analog thereof. Both cis- and trans-resveratrol glucoside (RGluc) were listed among the active agents, and the patent discloses these compounds as being either naturally occurring or chemically synthesized in the laboratory.

Subsequent to the epidemiological and biochemical studies which indicated that the resveratrol in wine was at least in part providing valuable protection against cardiovascular disease, numerous labs detected high levels of RGluc in several red and white wines. In view of these findings, it was reported that RGluc likely contributes to the human health benefit of wines (Goldberg, et al. 1996. :Resveratrol glucosides are important components of commercial wines," *Am J Enolog and Viticulture* 47:415–420).

The present invention describes transgenic plants and plant cells that have been modified to contain heterologous RGluc, as well as use of such plants or plant cells in manufacturing foods, nutritional supplements, animal feed supplements, nutraceuticals, and pharmaceuticals to serve as nutritional and therapeutic elements in human and animal diets.

BRIEF DESCRIPTION OF THE DRAWINGS

FIGS. 1A and 1B (SEQ ID NO:1) depict the sequence of the promoter+resveratrol synthase coding region+terminator cassette (HindIII partial digestion fragment) which was transferred into the HindIII site of the T-DNA region of pGA482, preparing it for *Agrobacterium*-based transfer to plant cells. FIG. 1A contains bases 1–1920, and FIG. 1B contains bases 1921–3089. HindIII restriction enzyme sites are found at bases 1 to 6 and 3084 to 3089 (indicated by "★"). A NcoI restriction enzyme site is found at bases 902 to 907 (indicated by "†"). A BamHI restriction enzyme site is found at bases 2849 to 2854 (indicated by "■"). Bases 1 to 901 contain the CaMV promoter (with duplicated enhancer element) and TEV untranslated region from pRTL2. Bases 902 to 2854 contain the NcoI (partial digest) and BamHI (complete digest) restriction enzyme generated fragment from the RS cDNA clone (indicated by underlining). Bases 904 to 2064 contain the coding region of the RS protein (indicated by italics), and the amino acid sequence is given in SEQ ID NO:2. Bases 2855 to 3089 contain the CaMV untranslated region from pRTL2.

FIG. 3A depicts RS transcript levels total RNA (10 μg/lane) extracted from leaves, internodes and roots of three independently transformed alfalfa lines (lanes 1–3) and one control line (C=pGA482 vector control plant). FIG. 3B depicts the same total RNA extracts hybridized with an alfalfa CHS cDNA probe. In both experiments (FIG. 3A and FIG. 3B), hybridization with an 18S ribosomal RNA probe (18S) served as a loading control.

FIG. 12A depicts a pGA482 vector control plant leaf at 10 days post-inoculation (CFU/ml=10,000). FIG. 12B depicts a transformed CaMV35S:RS RGluc-accumulating plant leaf at 10 days post-inoculation (CFU/ml=10,000). FIG. 12C depicts trypan blue staining of the inoculated control line showing numerous pycnidia (dark roundish spots) and hyphae (thin dark lines radiating outward from inoculation hole). Wound-inoculated leaves were detached from stems after 10 days then placed at 100% relative humidity for three days before staining. FIG. 12D depicts trypan blue staining of the inoculated CaMV35S:RS RGluc-accumulating line showing no pycnidia or hyphae beyond the inoculation wound site. Wound-inoculated leaves were detached from stems after 10 days then placed at 100% relative humidity for three days before staining.

SUMMARY OF THE INVENTION

Figure 2:
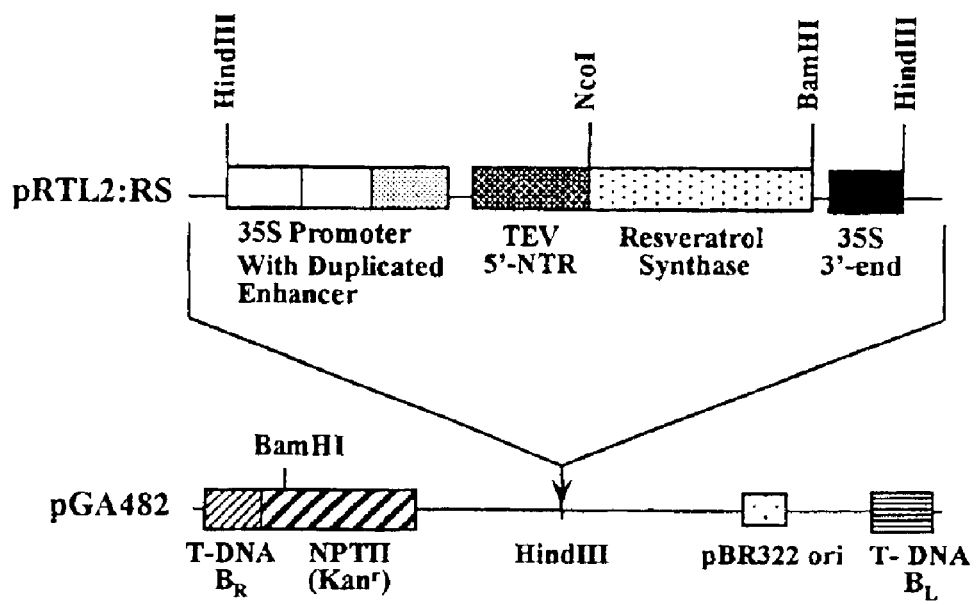
FIG. 2 is a schematic drawing of the vector constructs used in this method: double CaMV35S:RS binary vector containing a resveratrol synthase CDNA from peanut.

In one aspect, the present invention is a food comprising edible transgenic plant material capable of being ingested for its nutritional value, wherein the transgenic plant is transformed with a portion of a resveratrol synthase gene and exhibits increased levels of resveratrol glucoside when compared to levels of resveratrol glucoside in plants of the same species which do not comprise the portion of a resveratrol synthase gene. The transgenic plant can be transformed with a resveratrol synthase gene construct. Exemplary transformed plants include legumes. Exemplary legumes include alfalfa and soybean.

In another aspect, the present invention is a food comprising resveratrol glucoside isolated from an edible transgenic plant which is transformed with a portion of a resveratrol synthase gene and exhibits increased levels of resveratrol glucoside when compared to levels of resveratrol glucoside in plants of the same species which do not comprise the portion of a resveratrol synthase gene. The transgenic plant can be transformed with a resveratrol synthase gene construct. Exemplary transformed plants include legumes. Exemplary legumes include alfalfa and soybean.

In another aspect, the present invention is an edible composition comprising at least a portion of an edible transgenic plant which is transformed with a portion of a resveratrol synthase gene and exhibits increased levels of resveratrol glucoside when compared to levels of resveratrol glucoside in plants of the same species which do not comprise the portion of a resveratrol synthase gene, wherein the composition is suitable for ingestion as a food stuff, a nutritional supplement, an animal feed supplement, or a nutraceutical. The transgenic plant can be transformed with a resveratrol synthase gene construct. Exemplary transformed plants include legumes. Exemplary legumes include alfalfa and soybean.

In another aspect, the present invention is a composition comprising resveratrol glucoside suitable for administration as a food stuff, a nutritional supplement, an animal feed supplement, a nutraceutical, or a pharmaceutical, wherein the resveratrol glucoside is isolated from at least a portion of an edible transgenic plant which is transformed with a portion of a resveratrol synthase gene and exhibits increased levels of resveratrol glucoside when compared to levels of resveratrol glucoside in plants of the same species which do not comprise the portion of a resveratrol synthase gene. The transgenic plant can be transformed with a resveratrol synthase gene construct. Exemplary transformed plants include legumes. Exemplary legumes include alfalfa and soybean.

In another aspect, the present invention is an edible transgenic plant transformed with a portion of a resveratrol synthase gene, wherein the transformed plant exhibits increased levels of resveratrol glucoside when compared to levels of resveratrol glucoside in plants of the same species which do not comprise the portion of a resveratrol synthase gene. The transgenic plant can be transformed with a resveratrol synthase gene construct.

In another aspect, the present invention is seed from an edible transgenic plant transformed with a portion of a resveratrol synthase gene, wherein the transformed plant exhibits increased levels of resveratrol glucoside when compared to levels of resveratrol glucoside in plants of the same species which do not comprise the portion of a resveratrol synthase gene. The transgenic plant can be transformed with a resveratrol synthase gene construct.

In another aspect, the present invention is progeny from an edible transgenic plant transformed with a portion of a resveratrol synthase gene, wherein the transformed plant exhibits increased levels of resveratrol glucoside when compared to levels of resveratrol glucoside in plants of the same species which do not comprise the portion of a resveratrol synthase gene. The transgenic plant can be transformed with a resveratrol synthase gene construct.

In another aspect, the present invention is progeny from seed of an edible transgenic plant transformed with a portion of a resveratrol synthase gene, wherein the transformed plant exhibits increased levels of resveratrol glucoside when compared to levels of resveratrol glucoside in plants of the same species which do not comprise the portion of a resveratrol synthase gene. The transgenic plant can be transformed with a resveratrol synthase gene construct.

In another aspect, the present invention is a method of increasing the nutritional value of an edible plant by transforming the plant with a portion of a resveratrol synthase gene, wherein the transformed plant exhibits increased levels of resveratrol glucoside when compared to levels of resveratrol glucoside in plants of the same species which do not comprise the portion of a resveratrol synthase gene. The transgenic plant can be transformed with a resveratrol synthase gene construct.

In another aspect, the present invention is a method of using an edible transgenic plant transformed with a portion of a resveratrol synthase gene, wherein the plant exhibits increased levels of resveratrol glucoside when compared to levels of resveratrol glucoside in plants of the same species which do not comprise the portion of a resveratrol synthase gene, to provide a nutraceutical benefit to a human or animal administered the resveratrol glucoside. The transgenic plant can be transformed with a resveratrol synthase gene construct. Preferably, the resveratrol glucoside is administered by ingestion of at least a portion of the plant. Alternately, the resveratrol glucoside is administered by ingestion of a composition comprising resveratrol glucoside isolated from the plant.

In another aspect, the present invention is a method of using resveratrol glucoside isolated from an edible transgenic plant transformed with a portion of a resveratrol synthase gene, wherein the plant exhibits increased levels of resveratrol glucoside when compared to levels of resveratrol glucoside in plants of the same species which do not comprise the portion of a resveratrol synthase gene, to provide a pharmaceutical benefit to a patient administered the resveratrol glucoside. The transgenic plant can be transformed with a resveratrol synthase gene construct.

In another aspect, the present invention is a method for creating a transgenic plant comprising an increased level of resveratrol glucoside, comprising transforming a plant with a portion of a resveratrol synthase gene to form a transgenic plant, wherein the transgenic plant exhibits increased levels of resveratrol glucoside when compared to levels of resveratrol glucoside in plants of the same species which do not comprise the portion of a resveratrol synthase gene. Preferably, the plant is transformed by introducing an expression cassette comprising a transcribable DNA fragment, wherein the DNA fragment comprises resveratrol synthase cDNA. Exemplary transformed plants include legumes. Exemplary legumes include alfalfa and soybean.

In another aspect, the present invention is a method of increasing disease resistance in an edible plant by transforming the plant with a portion of a resveratrol synthase gene, wherein the transformed plant exhibits increased levels of resveratrol glucoside when compared to levels of resveratrol glucoside in plants of the same species which do not comprise the portion of a resveratrol synthase gene. The transgenic plant can be transformed with a resveratrol synthase gene construct.

In another aspect, the present invention is a method of decreasing spoilage of an edible plant or plant part after harvesting by transforming the plant or plant part with a portion of a resveratrol synthase gene, wherein the transformed plant or plant part exhibits increased levels of resveratrol glucoside when compared to levels of resveratrol glucoside in plants of the same species which do not comprise the portion of a resveratrol synthase gene. The transgenic plant can be transformed with a resveratrol synthase gene construct.

In another aspect, the present invention is an edible transgenic plant comprising at least one recombinant DNA sequence encoding a portion of a resveratrol synthase gene, wherein the plant, upon expression of the gene, exhibits increased levels of resveratrol glucoside when compared to levels of resveratrol glucoside in plants of the same species which do not comprise said recombinant DNA sequence.

In another aspect, the present invention is a seed from an edible transgenic plant comprising at least one recombinant DNA sequence encoding a portion of a resveratrol synthase gene, wherein the plant, upon expression of the gene, exhibits increased levels of resveratrol glucoside when compared to levels of resveratrol glucoside in plants of the same species which do not comprise the same recombinant DNA sequence.

In another aspect, the present invention is progeny from an edible transgenic plant comprising at least one recombinant DNA sequence encoding a portion of a resveratrol synthase gene, wherein the plant, upon expression of the gene, exhibits increased levels of resveratrol glucoside when compared to levels of resveratrol glucoside in plants of the same species which do not comprise the same recombinant DNA sequence.

In another aspect, the present invention is progeny from seed of an edible transgenic plant comprising at least one recombinant DNA sequence encoding a portion of a resveratrol synthase gene, wherein the plant, upon expression of the gene, exhibits increased levels of resveratrol glucoside when compared to levels of resveratrol glucoside in plants of the same species which do not comprise the same recombinant DNA sequence.

In another aspect, the present invention is the use of an edible transgenic plant transformed with a portion of a resveratrol synthase gene, wherein the plant exhibits increased levels of resveratrol glucoside when compared to levels of resveratrol glucoside in plants of the same species which do not comprise the portion of a resveratrol synthase gene, for the preparation of a nutraceutical preparation for achieving a nutritional effect. The transgenic plant can be transformed with a resveratrol synthase gene construct.

In another aspect, the present invention is the use of an edible transgenic plant transformed with a portion of a resveratrol synthase gene, wherein the plant exhibits increased levels of resveratrol glucoside when compared to levels of resveratrol glucoside in plants of the same species which do not comprise the portion of a resveratrol synthase gene, for the preparation of a pharmaceutical preparation for achieving a therapeutic effect. The transgenic plant can be transformed with a resveratrol synthase gene construct.

DETAILED DESCRIPTION

The present invention provides for transformation of plants or plant cells which do not normally accumulate stilbenes with a portion of a resveratrol synthase gene wherein the transgenic plants exhibit increased levels of resveratrol glucoside ("RGluc") when compared to levels of resveratrol glucoside in plants of the same species which do not comprise that same portion of a resveratrol synthase gene. Such plants include dicots and monocots, including but not limited to alfalfa, soybean, tomato, lettuce, tobacco, corn, maize, cotton, squash, beans and other legumes, melons, broccoli and other cole crops, stone fruits, citrus fruits, and strawberries. In the present invention, unless otherwise stated, as used herein, the term "plant" or "progeny" includes plant parts, plant tissue, plant cells, plant protoplasts, plant cell tissue cultures from which plants can be regenerated, plant calli, plant clumps, explants, plant cells that are intact in plants, or parts of plants, such as embryos, pollen, ovules, flowers, capsules, stems, leaves, seeds, roots, root tips, and the like.

A transgenic plant which has accumulated RGluc is useful in improving human and animal nutrition. Edible transgenic plants high in RGluc can be utilized as food for humans and animals. Edible compositions high in RGluc can also be made by incorporation of the transgenic plants or plant materials, or by incorporation of RGluc isolated from the transgenic plants. Compositions useful for administration as a food stuff, a nutritional supplement, an animal feed supplement, a nutraceutical, or a pharmaceutical can be made by incorporation of the truansgenic plants or plant materials, or by incorporation of RGluc isolated from the transgenic plants. The nutritional value of a plant can be increased by transforming the plant with a portion of a resveratrol synthase gene and, as a result, accumulating high amounts of RGluc in the plant. Disease resistance can be increased in the transgenic plant by the accumulation of high levels of RGluc upon expression of a resveratrol synthase gene. Likewise, spoilage of transgenic plants or plant parts can be decreased by the accumulation of high levels of RGluc upon expression of a resveratrol synthase gene.

Preferably, RGluc is administered orally by directly ingesting the transgenic plant. Alternatively, RGluc can be isolated from transgenic plants to be used as a crude extract or purified compound. Administration of transgenically produced RGluc to humans or animals provides enhanced pharmaceutical and nutraceutical effects, including but not limited to benefits received from an antioxidant, platelet aggregation inhibitor, arachidonate metabolism inhibitor, protein kinase inhibitor, inducer of apoptotic cell death in tumor cells, estrogen receptor antagonist, inhibitor of ribonucleotide reductase, tumor initiation inhibitor, tumor promotion inhibitor, tumor progression and differentiation inhibitor, inhibitor of COX-2 and COX-2 induction, lipoprotein synthesis and release modulator as well as other beneficial effects. Transgenically-produced RGluc is also useful as a ultraviolet light protectant, an ultra-violet stabilizer for biocontrol agents, and an agent in the storage of photochemical energy. Based upon RGluc's role in conferring resistance to plants against fungal pathogens, transgenically produced RGluc can also have applications as an antifungal and antibacterial agent in humans.

Transgenically produced RGluc confers disease resistance to heterologous plants that otherwise do not produce stilbenes or do not constitutively accumulate RGluc and do not, therefore, enjoy the benefits of stilbenes. A plant transgenically altered to comprise a resveratrol synthase gene can generate and accumulate RGluc prior to adverse conditions, including but not limited to infection by a pathogen. Thus, RGluc can be used to improve crop yield and quality of food and other plant products.

The structural differences between RGluc and free resveratrol provides increased chemical stability in RGluc. In particular, the glucose on the 3-hydroxyl of RGluc reduces the potential for oxidation of the aglycone by acting as a protecting group for this hydroxyl and reducing the oxidation potential of the dioxygenated ring, relative to the analogous portion of resveratrol. Consequently, RGluc is less subject to oxidation than is resveratrol. RGluc's decreased potential for oxidation provides advantages over resveratrol both in vitro and in vivo: (1) decreased oxidation by air resulting in increased storage stability in vitro; (2) decreased oxidation by peroxidases, oxygen, peroxides, and other processes in living plant cells, potentially resulting in improved disease resistance in transgenic plants; and (3) decreased oxidation by peroxidases, oxygen, peroxides, and other processes during consumption by humans or animals, potentially resulting in improved health benefits. In plants, glycosylated compounds are also stored in plant vacuoles, leading to further stability of RGluc against oxidation.

RGluc is also preferable to free resveratrol in human and animal diets. Under certain conditions, it is believed that RGluc can be biologically active, or can be readily hydrolyzed into the biologically active form. RGluc is readily convertible to resveratrol by beta-glucosidase, by other glucosidases, or by non-enzymatic hydrolysis, such as by acid hydrolysis. It is believed that RGluc will be absorbed in the digestive system as readily or more readily than free resveratrol, as is the case for numerous sugar derivatives of pharmaceuticals in comparison to the corresponding aglycones. It is further believed that RGluc is hydrolyzed to free resveratrol before or after absorption in the mammalian digestive tract. Therefore, plants which contain RGluc provide a stable dietary source of resveratrol.

The methods of producing RGluc from transgenic plants or cells from transgenic plants as presented herein provide advantages over production methods which utilized non-transgenic plants in which RGluc occurs naturally. Few RGluc-producing nontransgenic plants have been identified, and of these, many are not appropriate for general human or animal consumption. The present invention expands RGluc production to a wide variety of edible plants, resulting in (1) increased sources for the procurement of RGluc producing plants; (2) a larger growing region for RGluc-producing plants which potentially leads to increased production; (3) reduction in seasonal and/or climate limitations associated with nontransgenic RGluc-producers; and (4) increased consumer satisfaction.

In the present invention, a plant which does not normally accumulate stilbenes is transformed with a portion of a resveratrol synthase gene, leading to the uptake of a DNA fragment comprising the resveratrol synthase coding region from either a resveratrol synthase (RS) cDNA or genomic clone, and subsequent generation of RGluc in the plant. In the present invention, whole plants or tissue explants can be transformed. Transformed cells can be fully regenerated into intact plants or cultured as plant cell callus cultures, or plant cell suspension cultures.

In general, an RS coding region is selected. Resveratrol synthase cDNAs useful in the present invention can be obtained from mRNA isolated from any natural source. For example, a cDNA from peanut can preferably be used to generate RGluc. Any plant known to produce resveratrol, RGluc, or other resveratrol derivatives may also serve as sources of suitable cDNAs, or coding sequences may be synthesized in vitro based on available sequences for resveratrol synthases. Coding regions may also be obtained from genomic DNA, including or omitting intron sequences. Accumulation of RGluc is favored in plant tissues which contain the necessary biosynthetic precursors and low levels of β-glucosidases. Such conditions may be found in any plant cell, but are more likely to be present in non-stressed tissues, such as leaves constantly expressing RS driven by a constitutive promoter, rather than wounded or infected tissues which contain, release, or induce β-glucosidases.

Preferably, a resveratrol construct is made by subcloning an RS cDNA into a promoter cassette. Any promoter compatible with the selected RS cDNA can be used in the vector constructs of the present invention. It is also believed that a promoter within the plant cell which is capable of initiating transcription of the RS cDNA can be utilized, if the RS gene is integrated into the plant genome downstream of a transcription start site. Promoters which drive high levels of transcription in biosynthetically active plant cells during all stages of development are most likely to produce maximum levels of RGluc. For production of RGluc in plant tissues for direct human consumption, promoters must be selected to drive expression in edible portions of the plants. Upstream (5') and downstream (3') untranslated sequences must also be included to ensure sufficient translation initiation and transcript processing (polyadenylation); these sequences can be derived from RS cDNAs or genomic clones, or from commonly available plant genes and transformation vectors.

The resulting transgene cassette is subsequently introduced into the plant cell where it is integrated into the plant cell genome. For *Agrobacterium*-mediated transformation, the resveratrol construct is subcloned into a binary vector. The resveratrol coding region and other elements of the construct will be inserted between the right and left borders of the T-DNA region of the binary vector, i.e., the borders which define the DNA sequences that will be transferred from the *Agrobacterium* to the plant cells. For *Agrobacterium tumefaciens*-mediated transformations, leaf disc transformation and regeneration methods are preferred, but other methods such as vacuum infiltration of plants are also possible. The same binary vectors can be used for *Agrobacterium rhizogenes*-mediated transformation, resulting in transformed cells, hairy roots, or regenerated plants. Other methods of introducing the transgene cassette into the living plant cell can be used, including but not limited to; biolistic particle bombardment, pollen transformation; protoplast electroporation; or permneabilization.

Several methods known in the art can be used to distinguish the progeny exhibiting stable inheritance of the transgene. For transgenic plants wherein the transgenic cassette contains both the RS cDNA and a gene coding for a visible phenotypic change, the selection can be based upon visual examination of the progeny. For plant transformations involving a selectable marker gene, the appropriate selectable agent can be applied to the plants to select the transformants. Optionally, Southern blot analysis or PCR analysis can be used to verify the presence of the transferred gene in the genome of the transformed plants. RNA gel blot analysis, RT-PCR, or similar techniques can be used to verify the transcription of the RS gene in transformed tissues. Progeny which are stably transformed with the RS construct and successfully accumulating RGluc can be identified by chemically analyzing the plant tissues for the presence of RGluc, using chemical methods including but not limited to organic extraction followed by high pressure liquid chromatography (HPLC), gas chromatography (GC), gas chromatography-mass spectrometry (GC-MS), or capillary electrophoresis (CE).

RGluc can be extracted from the plant tissue with organic solvents such as acetone or methanol or expressed from the tissues as a crude sap exudate. RGluc-containing plants, plant parts or cells can also be used in their fresh, frozen or dried form.

EXAMPLE 1

Transformation of Alfalfa with Peanut RS CDNA

Alfalfa was transformed using a peanut RS cDNA, and the resulting transgenic plants were investigated.

Plant Material and Greenhouse Conditions

Alfalfa (*Medicago saliva* L.) c.v. Regen SY (Bingham, et al. 1991 "Regeneration of alfalfa hybrid Regen-Sy germplasm from tissue culture and transformation research," *Crop Sci* 31:1098) stocks and transgenic lines were maintained in greenhouse conditions under a 16 hour photoperiod in MetroMix 350 (The Scotts Co., Marysville, Ohio). Independent transgenic lines were vegetatively propagated by cuttings, planted in MetroMix 350 in growth chambers (Conviron, Winnipeg, Manitoba, Canada) under a 16 hour photoperiod with 100% relative humidity for 3 weeks.

Vector Constructs and Plant Transformation

The peanut (*Arachis hypogaea*) resveratrol synthase (RS) CDNA (nucleotides 902 to 2854 of SEQ ID NO:1 and FIGS. 1A and 1B) (Tropf, et al. 1994. "Evidence that stilbene synthases have developed from chalcone synthases several times in the course of evolution,"*J Mol Evol* 38:610–618) was subcloned into the NcoI and BamHI sites of a CaMV-35S dual enhancer promoter cassette pRTL2 (Restrepo, et al. 1990. "Nuclear transport of plant polyviral proteins," *Plant Cell* 2:987–998). The CaMV-35S:RS cassette was partially digested with HindIII (SEQ ID NO:1 and FIG. 1A and 1B) and subcloned into the HindIII site of the binary vector pGA482 (FIG. 2). Restriction enzyme digest and DNA sequencing confirmed the integrity of the construct. The binary vector and vector constructs were maintained in *E. coli* DH5I_(Clontech, Palo Alto, Calif.) and transferred by electroporation to *Agrobacterium tumefaciens* LBA4404.

Transgenic alfalfa plants were generated from the transformation and regeneration-competent alfalfa (c.v. Regen SY) (Bingham, et al. 1991. *Crop Sci* 31:1098) following a modified version of published procedures (Bingham, et al. 1975. "Breeding alfalfa which regenerates from callus tissue in culture," *Crop Sci* 15:719–721). In the modified procedure, alfalfa plants were transformed with *Agrobacterium* strain LBA4404 harboring either the pGA482 (control) or the CaMV-35S:RS construct by leaf disc method with regeneration under kanamycin selection (Oommen, et al. 1994. "The elicitor-inducible alfalfa isoflavone reductase promoter confers different patterns of developmental expression in homologous and heterologous transgenic plants," *Plant Cell* 6:1789–1803). Surviving plantlets were placed on MS media without selection (Murashige, T. and Skoog, F. 1962. "A revised media for rapid growth and bioassay with tobacco tissue culture," *Physiol Plant* 15:473–497) for an additional month before transfer to Magenta boxes (Magenta Corp. Chicago, Ill.) and subsequent propagation by vegetative cuttings. Rooted cuttings were transferred to MetroMix 350, placed on a misting bench for one week, and finally placed under greeenhouse conditions.

Southern Blot and PCR Analyses of Transgenic Lines

Genomic DNA was extracted from 1 gram of alfalfa green leaf tissue as described (Dellaporta, et al. 1983. "A plant DNA minipreparation: version II," *Plant Mol Biol Rep* 1:19–21). Twenty micrograms of DNA were digested with HindIII and size fractionated by 1% agarose gel electrophoresis (Sambrook, et al. 1989. *Molecular Cloning. A Laboratory Manual*, $2^{nd}$ ed., Cold Spring Harbor Laboratory Press). The gel was treated in 0.25 M HCl for ten minutes, denatured with 0.5 M NaOH/1.0 M NaCl for twenty minutes and neutralized with 0.5 M Tris-HCl/1.5 M NaCl for twenty minutes with gentle shaking and then transferred overnight by capillary action to a nylon membrane (GeneScreen Plus, DuPont, Boston, Mass.) in 5×SSPE (1×SSPE is 0.15 M NaCl, 10 mM sodium phosphate, 1 mM EDTA, pH 7.4). The DNA was covalently crosslinked to the membrane by ultraviolet light (Stratalinker, Stratagene, La Jolla, Calif.). The hybridization probe was prepared by digesting the pGA482 binary vector with BamHI and HindIII to release a fragment of NPTII gene. The gel-purified fragment was labeled with $^{32}$P-dCTP via the random primer method (Prime a Gene, Promega, Madison, Wis.). Southern hybridizations were carried out by the method of Church and Gilbert (Church, G. M. and Gilbert, W. 1984. "Genomic sequencing," *Proc Natl Acad Sci USA* 81:1991–1994) at 65° C. Independent transformants were subsequently identified by the hybridization pattern. All independent transgenic plants examined contained only one copy of the transgene cassette.

To identify those independent transgenic lines that successfully integrated the full length coding region, RS cDNA specific primers 5' CCATGGAAGGGGGAATTCGC 3' (SEQ ID NO:3) and 5' GAGCCATTCAGCACCTTAGC 3' (SEQ ID NO:4) were used in PCR reactions. One to two micrograms of genomic DNA were combined with 0.4 μM (final concentration) of primers, 10nM dNTPs, 1 unit of Taq-DNA polymerase (Promega, Madison, Wisc.), in 1X PCR reaction buffer adjusted to a final volume of 50 microliters. The binary vector construct used in the transformation protocol served as a positive control reaction. Thermocycler (Singleblock System, Ericomp, Inc., San Diego, Calif.) conditions were as follows: denature at 95° C. for 2 minutes, anneal at 55° C. for 1.3 minutes, elongate at 72° C. for 2 minutes for a total of 30 cycles, followed by a final elongation of 15 minutes at 72° C. Twenty five microliters of PCR reaction products were separated by agarose gel electrophoresis and visualized by ethidium bromide staining under UV light.

Northern Blot Analyses of RS and CHS Transcript Levels

Total RNA was extracted from the leaves, internodes or roots by the method of Logemann, et al. (Logemann, et al. 1987. "Improved method for isolation of RNA from plant tissues," *Anal Biochem* 163:16–20). After overnight precipitation, the protocol was modified such that the RNA was purified from the aqueous phase by the method of Zhou and Goldsbrough (Zhou, J. and Goldsbrough, P. B. 1993. "An Arabidopsis gene with homology to glutathione S-transferase is regulated by ethylene," *Plant Mol Biol* 22:517–523). The RNA (10 μg/lane) was size fractionated by 1% agarose-formaldehyde gel electrophoresis by the method of Sambrook, et al. (Sambrook, et al. 1989. *Molecular Cloning. A Laboratory Manual*, $2^{nd}$ ed., Cold Spring Harbor Laboratory Press). The RNA was transferred overnight by capillary action to a nylon membrane (GeneScreen Plus, DuPont, Boston, Mass.) in 5X SSPE. The hybridization conditions and radio-labeling of probes were prepared as described in the previous section. For individual experiments, probes included a resveratrol synthase cDNA from peanut (Tropf, et al. 1994. *J Mol Evol* 38:610–618), a chalcone synthase cDNA (Junghans, et al. 1993. "Stress responses in alfalfa (*Medicago sativa* L.) 15. Characterization and expression patterns of members of a subset of the chalcone synthase multigene family," *Plant Mol Biol*22:239–253) and hybridized with the plant 18S ribosomal RNA probe (Eckenrode, et al. 1985. "Comparison of the nucleotide sequence of soybean 18S rRNA with the sequences of other small-subunit rRNAs," *J Mol Evol* 21: 259–269) as a loading control.

Figure 3A:
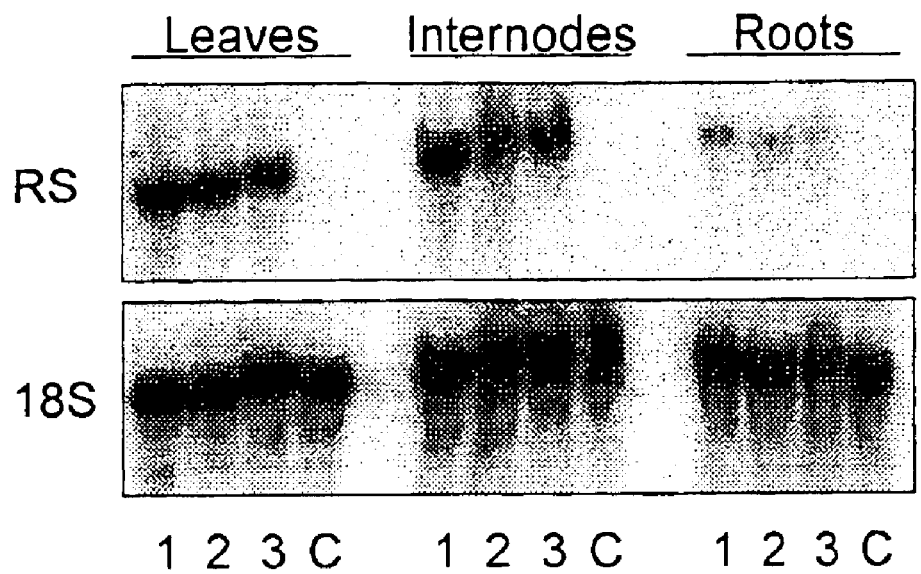
FIG. 3A and FIG. 3B are a composite photo of the autoradiogaphy results of Northern blot analysis (RNA get blot analysis) indicating comparative levels of resveratrol synthase (RS) to chalcone synthase (CHS) transcript levels in the leaves, internodes and roots.
Figure 3B:
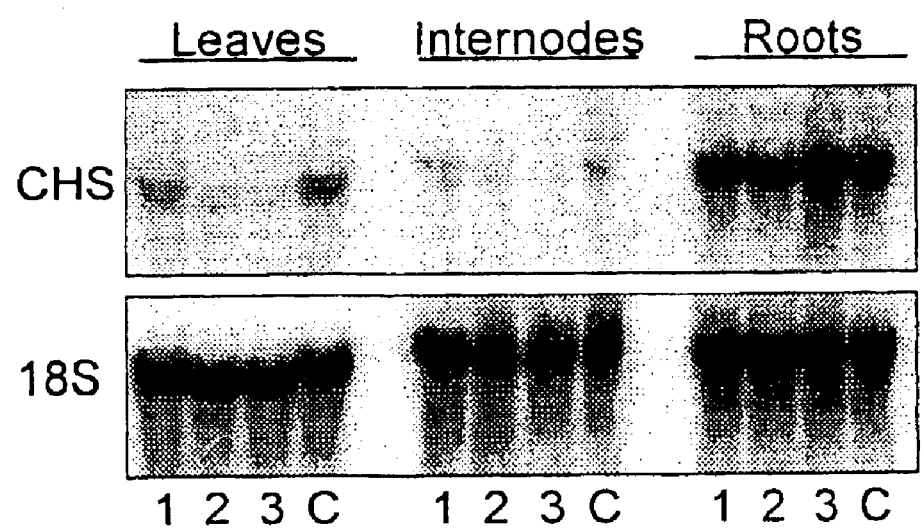

High levels of RGluc accumulate in the young leaves (approximately 150 μg/g fresh weight) and in the old internodes (approximately 130 μg/g fresh weight) of the highest accumulating alfalfa lines expressing RS. However, HPLC analyses of root extracts detected only marginal levels of RGluc (<2.0 μg/gram fresh weight) in these same independent lines (data not shown). Alfalfa roots are known to accumulate high constitutive levels of flavonoids and isoflavonoids (Oommen, et al. 1994. *Plant Cell* 6:1789–1803), and CHS would be a direct competitor of metabolic intermediates p-coumaroyl CoA and malonyl CoA. Therefore, northern blot experiments were performed to compare the relative transcript levels of RS and CHS in the leaves, internodes and roots of three independent CaMV35S:RS lines and a vector control line. Results in FIG. 3A and FIG. 3B show that the highest levels of RS transcripts are found in the leaves and internodes while comparatively low levels were detected in the roots (lanes 1–3). As expected, no RS transcripts were detected in the vector control (lane C)(FIG. 3A). In contrast, the highest CHS message levels were detected in the roots compared to the leaves and internodes (FIG. 3B). Therefore, the nearly undetectable levels of RGluc in the roots are due to a combination of relatively low RS transcript levels and strong competition for the available substrate pool of high levels of CHS.

Characterization and RGluc Identification by HPLC Analysis

Independent transgenic alfalfa lines harboring the CaMV35S:RS construct were analyzed for the presence of resveratrol by reverse phase C18 HPLC analyses (4.6×250 mm column, Baker, Phillipsburg, N.J.). Metabolites were extracted from 0.5–1.0 grams of fresh leaves, internodes or roots in 100% acetone for up to two days. The supernatant was dried completely under nitrogen and dissolved in 0.7 ml of methanol followed by 0.3 ml water. The sample was vortexed vigorously, sonicated for 5 minutes and then centrifuged to remove the insoluble debris. The final supernatant was concentrated to dryness then dissolved in 0.1 ml of methanol. For analysis, 20 μl of sample was injected and metabolites separated by a 45 minute linear gradient from 20–60% solvent B (solvent A=1.0% $H_3PO_4$, solvent B=100% acetonitrile) with a flow rate of 0.8 ml/min monitored at λ=320 nm. UV spectra of peaks of interest were recorded with a UV diode array detector (Beckman Instruments, Fullerton, Calif.). Characterization of the putative resveratrol-conjugate was performed by β-glucosidase digestion of a crude leaf extract. The methanol was removed under nitrogen and the residue dissolved in 200 μl of 25 mM citric acid/phosphate buffer (pH=5.2) containing 0.5 mg/ml β-glucosidase from almonds (Sigma Chemical Co., St. Louis, Mo.). After incubation at 37° C. for 1 hour, the free resveratrol was extracted from the aqueous phase 3 times with an equal volume of ethyl acetate. The ethyl acetate was pooled and concentrated to dryness under nitrogen, dissolved in methanol, and then analyzed by HPLC. The identity of resveratrol was confirmed by co-chromatography with a resveratrol standard (Sigma) and by comparison of UV absorbance spectra.

Figure 4:
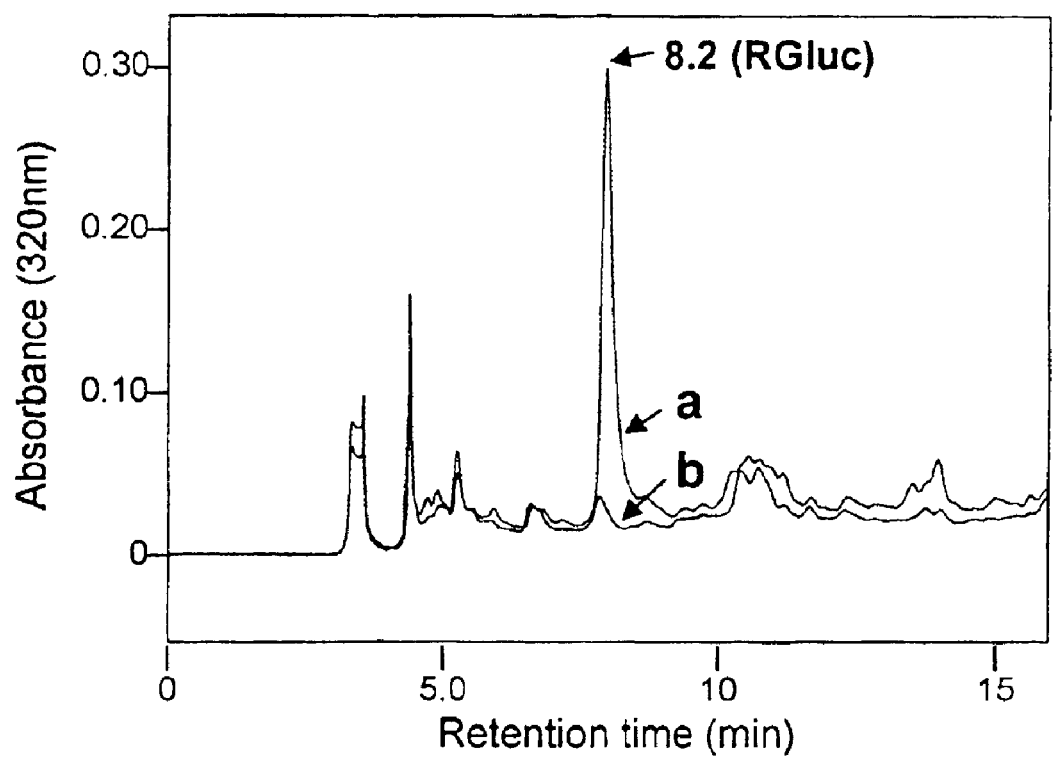
FIG. 4 is the data from the reverse phase (C18) HPLC analysis of crude acetone extracts of transgenic alfalfa plants revealing the unknown compound later identified as RGluc in the CaMV35S:RS transformed alfalfa line (chromatogram A) that is not present in a pGA482 binary vector control plant (chromatogram B). RGluc eluted at approximately 8.2 minutes under these conditions.
Figure 5:
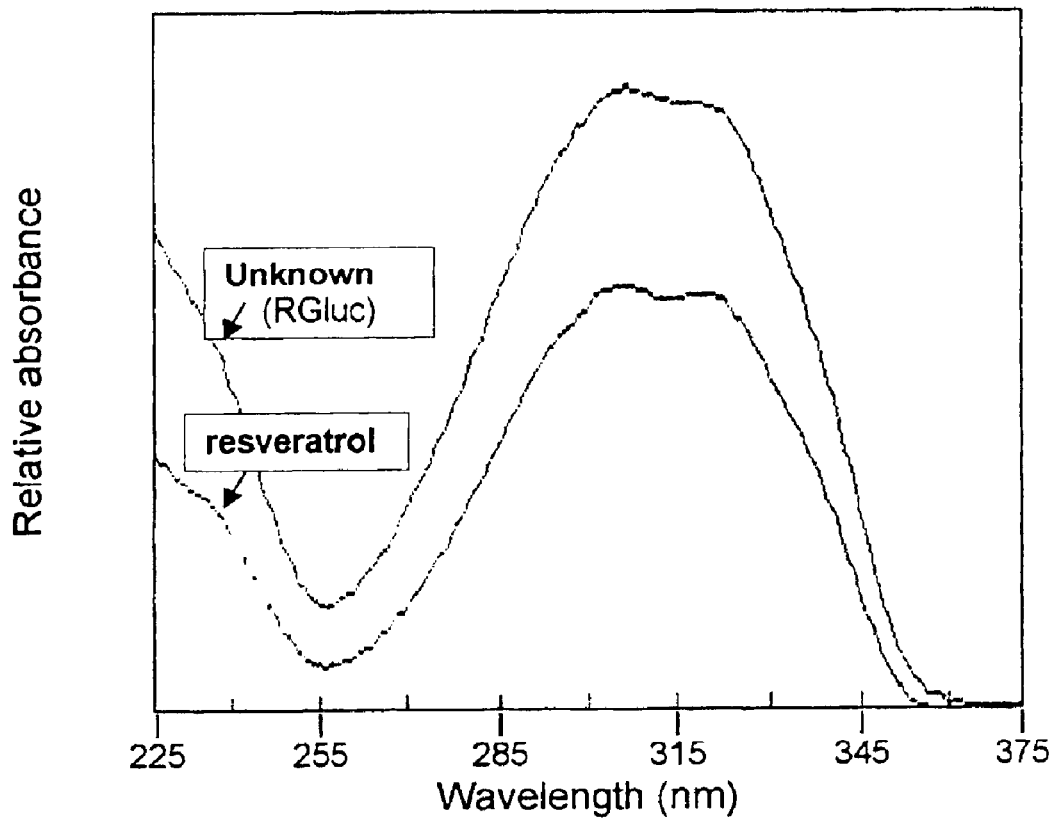
FIG. 5 is the UV absorbance spectra of the unknown compound later identified as RGluc compared to a known resveratrol standard.
Figure 6:
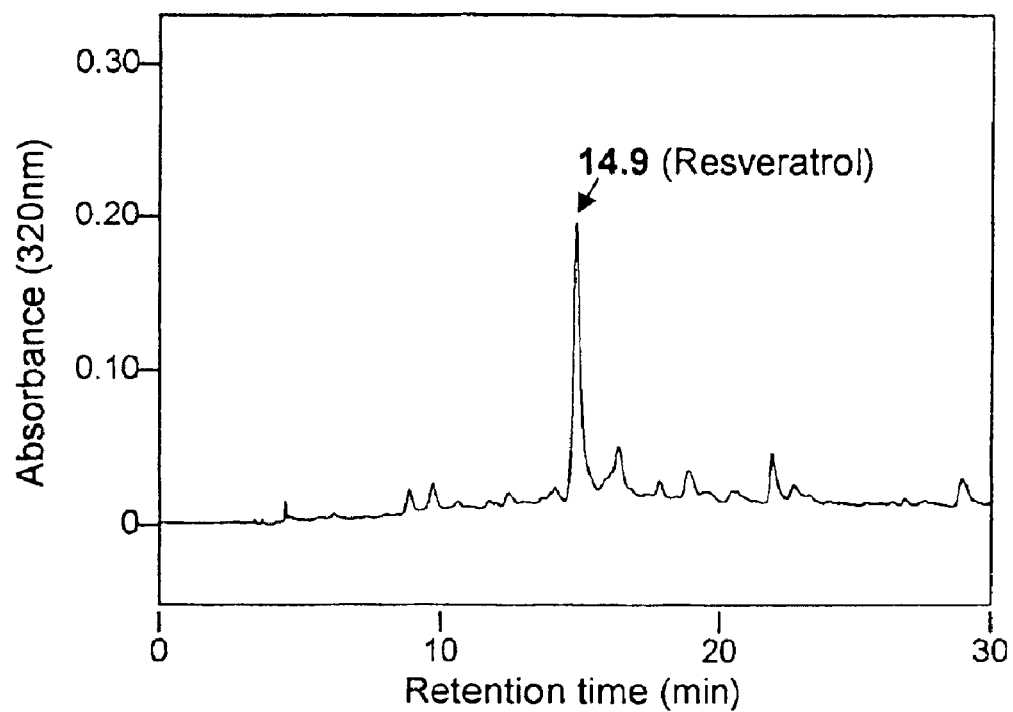
FIG. 6 is the HPLC chromatogram of the putative resveratrol-conjugate following treatment with beta-glucosidase revealing the release of the resveratrol aglycone. Identity was confirmed by co-chromatography with an authentic resveratrol standard.

Independent transgenic alfalfa lines harboring the CaMV35S:RS construct as evidenced by Southern blot and PCR analyses were analyzed by HPLC for the constitutive accumulation of resveratrol. Results shown in FIG. 4 reveal the presence of an unknown peak (8.2 minutes) that appears only in the leaves and internodes of lines transformed with the CaMV35S:RS binary vector (chromatogram A) and not vector control plants (chromatogram B). The UV spectra analysis of the 8.2 minute peak and a resveratrol standard are nearly identical with absorbance maxima of 307 nm and 320 nm for both compounds (FIG. 5). However, the 8.2 minute retention time is significantly less than the retention time observed with a resveratrol standard (14.9 minutes). This result shows that the resveratrol had been modified by the addition of hydrophilic moiety, possibly a sugar. Hydrolysis with β-glucosidase of the unknown compound results in the appearance of free resveratrol (FIG. 6). In addition, removal of $H_3PO_4$ from the aqueous phase of HPLC solvent system did not alter the retention time of the resveratrol conjugate (data not shown). This observation shows that the sugar moiety was not substituted with a charged group such as malonic acid.

$^1H$ and $^{13}C$ NMR Analyses of RGluc

The suspected resveratrol glucoside conjugate was purified from several kilograms of transgenic alfalfa leaves and internode tissue. Large volumes of crude acetone extracts were concentrated to near dryness under vacuum. Insoluble materials were removed by centrifugation with the remaining supernatant adjusted to 50% methanol. The extract was passed over C18 reverse phase disposable cartridge (SepPak, Waters Corp, Milford, Mass.) followed by concentration to near dryness under vacuum to remove the methanol. The aqueous phase was extracted 3 times with an equal volume of ethyl acetate. The ethyl acetate fractions were pooled and concentrated to dryness under vacuum. The final residue was dissolved in methanol. The resveratrol-conjugate was then purified by preparative C18 reverse phase HPLC (22.5 ×250 mm, Econosil, Deerfield, Ill.). For purification, 0.5 ml of extract was separated by a 45 minute linear gradient from 10–25% solvent B (solvent A=water, solvent B=acetonitrile) at a flow rate of 20 ml/minute monitored a λ=320 nm. Fractions containing the resveratrol conjugate were pooled, concentrated to dryness under nitrogen and purified a second time. The final fraction was concentrated to dryness and dissolved in a small volume of methanol. The concentration was estimated by comparison of the absorbance spectra to a known concentration of the resveratrol standard. The sample to be analyzed was dried under nitrogen and analyzed by $^{13}C$ NMR (150 MHz, $CD_3OD$) and $^1H$ NMR (600 MHz, $CD_3OD$). Identity was confirmed by comparison to previously published reports (Mattivi, et al. 1995. *J Agric Food Chem* 43:1820–1823; Waffo-Teguo, et al. 1998. *J Nat Prod* 61:655–657).

Data obtained from $^{13}C$-NMR and $^1H$-NMR given in Tables I and II below were highly consistent with previous reports which identified this compound as trans-resveratrol-3-O-β-glucopyranoside, commonly known as piceid or polydatin (Waterhouse, A. L. and Lamuela-Reventost, R. M. 1994. "The occurrence of piceid, a stilbene glucoside in grape berries," *Phytochemistry* 37:571–573; Mattivi, et al. 1995. *J Agric Food Chem* 43:1820–1823; Waffo-Teguo, et al. 1998. *J Nat Prod* 61:655–657). Table I contains $^{13}C$ NMR values for the RGluc purified from transgenic alfalfa (in column RS-X) compared with published values for resveratrol glucoside purified from two non-transgenic plants (Waffo Teguo, et al. 1998. "Isolation, identification, and antioxidant activity of three stilbene glucosides newly extracted from Vitis vinifera cell cultures," *J Nat Prod* 61:655–657; and Mattivi, et al. 1995. "Isolation, characterization, and evolution in red wine vinification of resveratrol monomers," *J Agri Food Chem* 43:1820–1823). Table II contains proton NMR values for the RGluc purified from transgenic alfalfa (in column RS-X) compared with published values for resveratrol glucoside purified from a non-transgenic plant (Waffo Teguo, et al. 1998. *J Nat Prod* 61:655–657).

In preliminary experiments, HPLC analyses of shoots collected from independent transgenic alfalfa lines found that the concentrations of RGluc ranged

TABLE I

Comparison of $^{13}C$-NMR Chemical Shift Values (150 MHz, $CD_3OD$) for Isolated Resveratrol Conjugate with Values from Two Published Studies

| $C^a$ | δ(RGluc) | $δ^b$ | $δ^c$ |
|---|---|---|---|
| 1 | 141.43 | 141.4 | 140.9 |
| 2 | 107.05 | 107.0 | 106.2 |
| 3 | 160.47 | 160.5 | 160.2 |
| 4 | 104.13 | 104.1 | 103.9 |
| 5 | 159.58 | 159.6 | 159.4 |
| 6 | 108.38 | 108.4 | 108.2 |
| 7 | 126.69 | 126.7 | 126.5 |
| 8 | 129.99 | 130.0 | 129.9 |
| 1' | 130.34 | 130.3 | 130.0 |
| 2',6' | 128.91 | 128.9 | 128.9 |
| 3',5' | 116.50 | 116.5 | 116.4 |
| 4' | 158.47 | 158.5 | 158.2 |
| Glucose | | | |
| 1" | 102.43 | 102.4 | 102.1 |
| 2" | 74.97 | 75.0 | 74.8 |
| 3" | 78.07 | 78.1 | 78.1 |
| 4" | 71.51 | 71.5 | 71.5 |
| 5" | 78.25 | 78.3 | 77.8 |
| 6" | 62.62 | 62.6 | 62.8 |

[a]Carbon assignments as reported by Mattivi et al.
[b]Values reported by Teguo et al. (1996).
[c]Values reported by Mattivi et al. (1995).

TABLE II

Comparison of $^1H$-NMR chemical shift values (600 MHz, $CD_3OD$) for the isolated resveratrol conjugate with published values

| Proton Assignment (Teguo)[a] | δ(RGluc) | $δ^b$ |
|---|---|---|
| H-2', H-6' | 7.35(2H, d) | 7.35(2H, d) |
| H-8 | 7.01(1H, d) | 7.00(1H, d) |
| H-7 | 6.84(1H, d) | 6.84(1H, d) |
| H-2 | 6.78(1H, br s) | 6.78(1H, br s) |
| H-3', H-5' | 6.76(2H, d) | 6.76(2H, d) |
| H-6 | 6.61(1H, br s) | 6.61(1H, br s) |
| H-4 | 6.45(1H, br s) | 6.44(1H, br s) |
| Glc H-1" | 4.89(1H, d) | 4.88(1H, d) |
| Glc H-6a" | 3.92(1H, dd) | 3.92(1H, dd) |
| Glc H-6b" | 3.71(1H, dd) | 3.70(1H, dd) |
| Glc H-2", H-3", H-4", H-5" | 3.48–3.38(4H, m) | 3.48–3.38(4H, m) |

Figure 7:
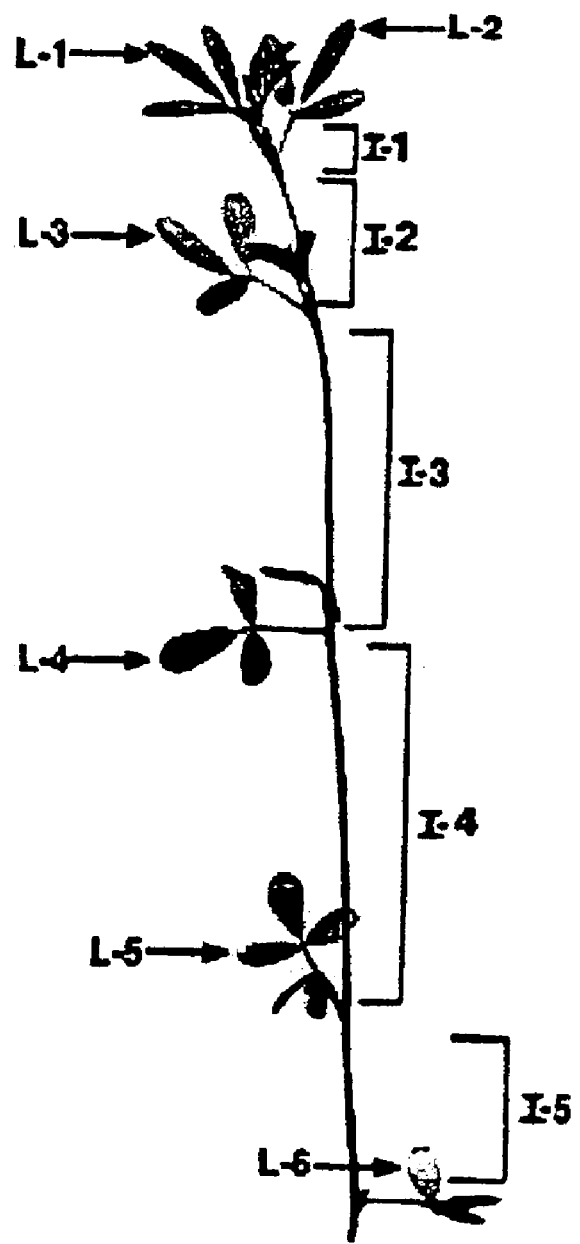
FIG. 7 depicts a representative alfalfa shoot labeled to illustrate leaf and internode designation used in the analysis of CaMV35S:RS transformed lines (L=leaves; I=internodes).
Figure 8:
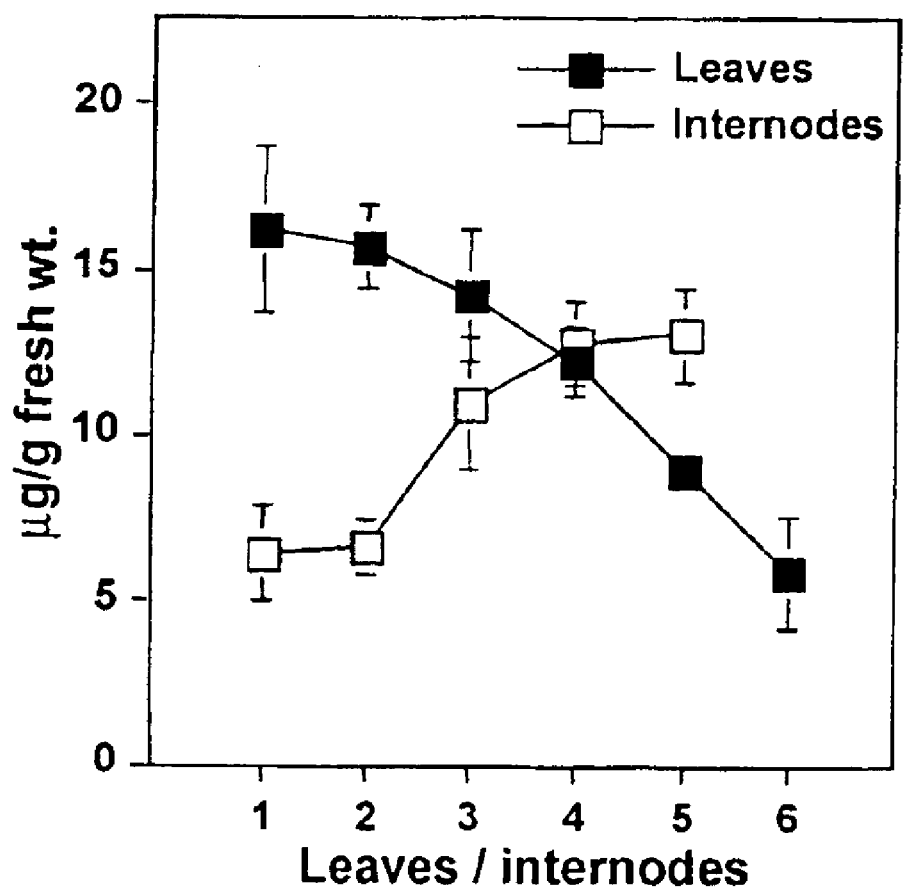
FIG. 8 is a graph of the results from HPLC quantitation of RGluc in leaves and internodes along shoots from a CaMV35S:RS transformed line revealing the age-and tissue-dependent accumulation of RGluc represented in terms of microgram resveratrol aglycone equivalents per gram of tissue.
Figure 9:
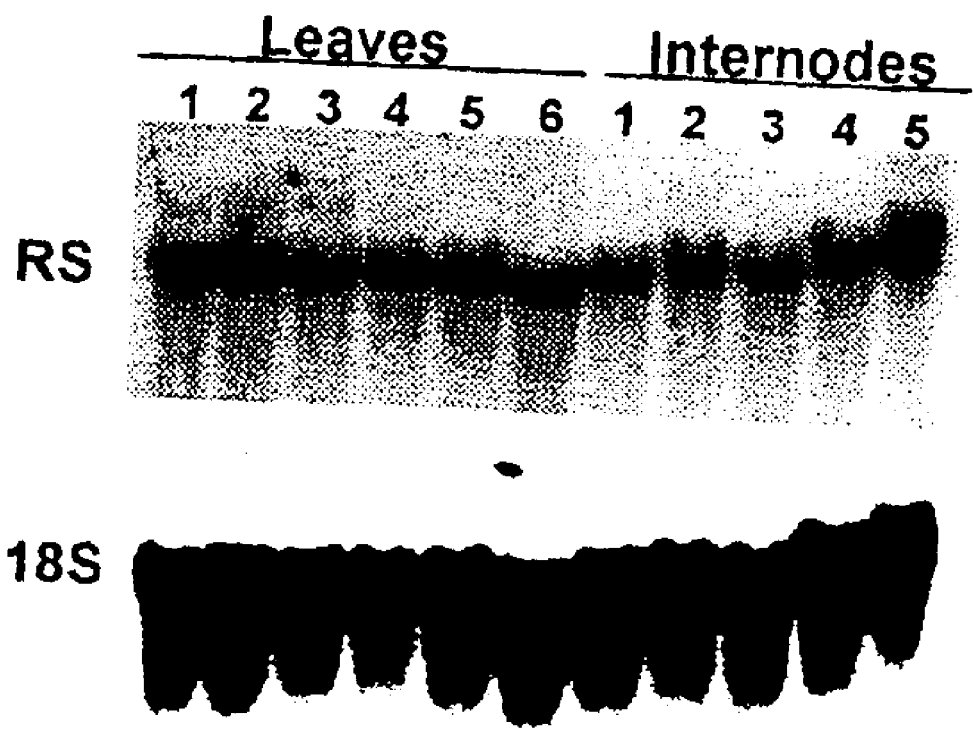
FIG. 9 is a composite photo of the autoradiography results of Northern blot analysis (RNA gel blot analysis) indicating resveratrol synthase (RS) transcript levels in the leaves and internodes relative to the age or tissue type, compared to an 18S ribosomal RNA probe (18S) served as a locating control (total RNA=10 µg/lane), indicating that the RS cDNA transcript is produced in all of these transgenic alfalfa tissues.

[a]Proton assignments as reported by Teguo et al. (1996)
[b]Values reported by Teguo et al. (1996).

from 5.0–20.0 μg/gram fresh weight, measured as resveratrol equivalents. However, these data were significantly variable for replicate samples taken from the same independent lines. Therefore, an experiment was performed to test whether the concentration of the RGluc was developmental or tissue dependent. Independent alfalfa lines that showed consistently high levels of RGluc were grown under greenhouse conditions. The leaves and internodes from several shoots were harvested, pooled and extracted for HPLC analysis according to their relative age and position on individual alfalfa shoots For example, L-1 was considered the youngest leaf (FIG. 7). Results show that the concentration of RGluc in the leaves declines significantly from the youngest to the oldest leaves on a µg/gram fresh weight basis (FIG. 8). In contrast, the concentrations increase significantly from the youngest internodes to the oldest. Similar results were obtained in two additional RGluc-accumulating lines (data not shown). Northern blot analyses taken from the same independent line indicated that the relative level of RS transcripts were not significantly affected by the age or tissue type (FIG. 9). Taken together, these data demonstrate there is no correlation between RS transcript levels and extractable levels of RGluc in these tissues. The concentration of RGluc in these tissues is dependent upon the relative availability of metabolic intermediates, p-coumaroyl CoA and malonyl CoA.

Agar-plate Bioassay and Plant-pathogen Interactions

The alfalfa fungal pathogen *Phoma medicaginis* Malbr. & Roum. var. *medicaginis* (Leath, K. T., "Spring black stem and leaf spot." In *Compendium of Alfalfa Diseases*, D. L. Stuteville & D C Erwin, 2$^{nd}$ ed., American Phytopathological Society Press, 1990, p.16–17) maintained on potato dextrose agar (PDA, Difco Laboratories, Detroit, Mich.) for one month in a dark growth chamber at 22° C. Agar-plate bioassays were performed by dissolving resveratrol or RGluc purified from transgenic alfalfa lines in 50 µl of ethanol. The concentration of RGluc (measured in resveratrol equivalents) was estimated by HPLC analysis and comparison to a known concentration of a resveratrol standard. The ethanol solution was added to molten PDA such that the final molar concentrations of resveratrol or RGluc were 0.18 mM (50 µg/ml resveratrol or 85 µg/ml for RGluc). For this experiment, control plates were made whereby an equal volume of ethanol was added to PDA without resveratrol. A small agar plug of *P. medicaginis* was placed in a petri dish containing the resveratrol-PDA mixture, sealed with parafilm and placed in a dark grown chamber at 22° C. The extent of hyphal growth was measured after one week.

To test for resistance in the transgenic lines, the first and second trifoliate leaves of greenhouse grown transgenic alfalfa lines were wound inoculated with a 27.5 gauge syringe needle dipped in a *P. medicaginis* spore suspension. The number of colony forming units per ml (CFU/ml) was estimated by plating a serial dilution of the spore suspension on PDA. After inoculation, the stem was cut at the fourth internode and placed in a magenta box, with the cut end imbedded in 0.8% water agar (Phytagar, Difco, Detroit, Mich.). The magenta box was sealed with parafilm to maintain 100% humidity and placed in a growth room (16 hour photoperiod, 22° C.) where disease symptoms were allowed to develop for 8 to 10 days. The extent of necrosis around the wound sites was measured with a digital video imaging system (Ultra-Lum, Inc., Paramount, Calif.) and analysis software (Scion Image for Windows, Frederick, Md.).

To determine the extent of hyphal growth and the formation of reproductive structures, excised leaves were place in 100% humidity for up to three days followed by staining with a trypan blue/ethanol solution (Keogh et al. 1980. "Comparison of histological and physiological responses to *Phykospora pachyrhizi* in resistant and susceptible soybeans," *Trans Br Mycol Soc* 74:329–333). Briefly, the leaves were completely covered with the trypan blue staining solution (10 ml lactic acid; 10 ml Tris-equilibrated phenol, pH 7.4; 10 ml glycerol; 10 ml water, 10 mg trypan blue; Sigma) followed by an equal volume of 100% ethanol. The samples were boiled for five minutes, and then allowed to cool at room temperature for up to 24 hours. For destaining, the staining solution was discarded, 0.8 g/ml of chloral hydrate was added followed by boiling for three minutes. The chloral hydrate was discarded, and the leaves rinsed well with water and stored in 50% glycerol solution. Fungal hyphae and pycnidia were examined with a dissecting microscope Model SMZ-10, Nikon, Japan) and photographed with Ektachrome 160T color slide film (Eastman Kodak, Rochester, N.Y.) with a Nikon FX-35WA 35 mm camera.

Prior to the transformation experiments, agar-plate bioassays were used to test a resveratrol standard for anti-fungal activity against several alfalfa pathogens. Results showed that an isolate of *Phoma medicaginis* was the most sensitive (data not shown). RGluc was purified by preparative HPLC from transgenic lines and tested in agar plate bioassays in order to assess its effectiveness against this same isolate. Results showed that hyphal growth was significantly reduced (>50%) in the presence of RGluc (85 µg/ml) or resveratrol (50 µg/ml). Three replicates of this experiment were performed. Importantly, the concentration of RGluc determined by HPLC analysis of the transgenic alfalfa lines is significantly higher to that used in these bioassays. Therefore, a sufficient concentration of RGluc should be available to inhibit pathogen ingress and reduce disease symptoms.

Figure 10:
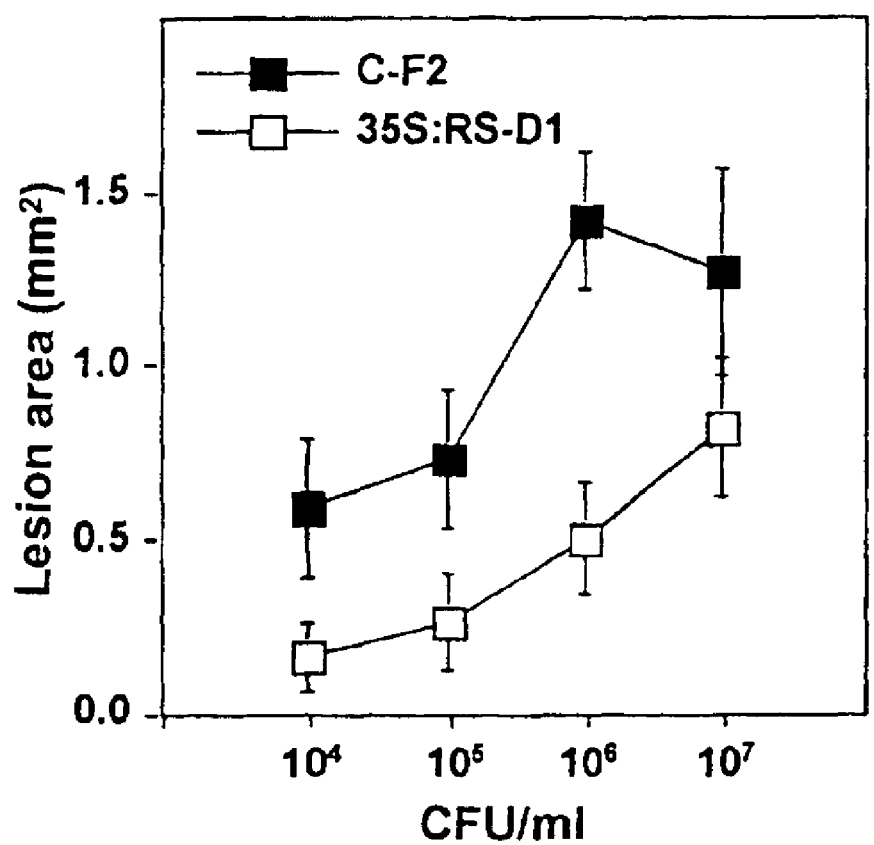
FIG. 10 is a graph depicting the quantitation of necrotic lesion area in leaves of control (pGA482-transformed plant C-F2) and RGluc-accumulating (CaMV 35S-RS construct transformed plant 35S:RS-D1) plants after wound-inoculation with the alfalfa fungal pathogen *Phoma medicaginis*. The points show the average necrotic lesion size (mm$^2$) surrounding the wound site at four different inoculum levels (CFU/ml) measured at 10 days post-inoculation in the transformed CaMV35S:RS and pGA482 vector control plants. The error bars represent the standard deviation of the mean.
Figure 11:
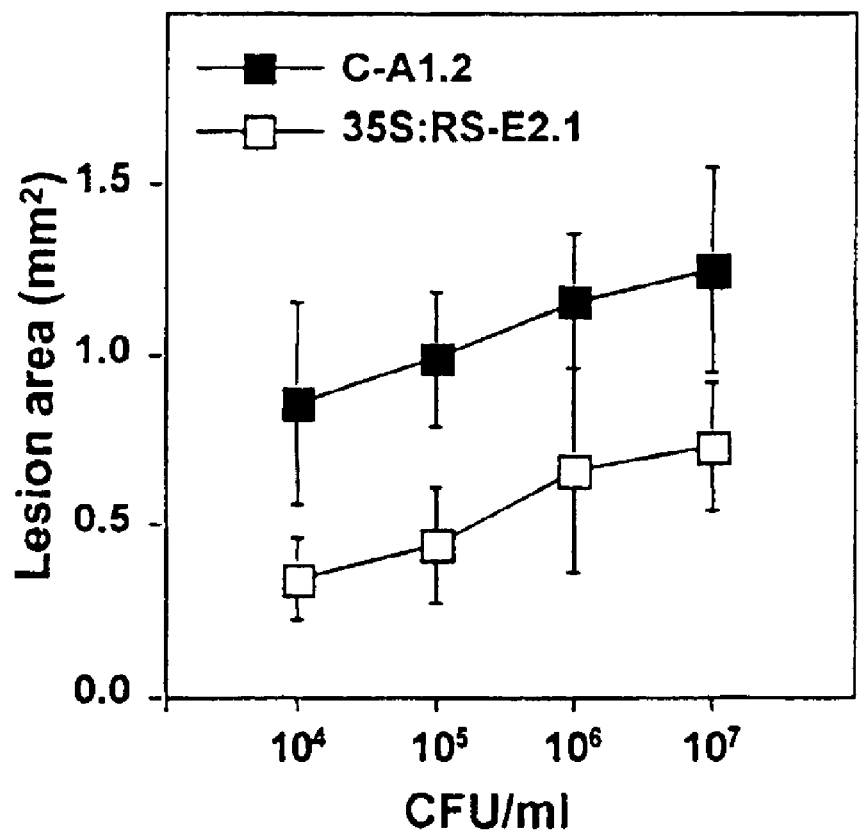
FIG. 11 is a graph depicting the quantitation of necrotic lesion area in leaves of control (pGA482-transformed plant C-A1.2) and RGluc-accumulating (CaMV35S-RS construct transformed plant 35S:RS-E2.1) plants after wound-inoculation with the alfalfa fungal pathogen *Phoma medicaginis*. The points show the average necrotic lesion size (mm$^2$) surrounding the wound site at four different inoculum levels (CFU/ml) measured at 10 days post-inoculation in the transformed CaMV35S:RS and pGA482 vector control plants. The error bars represent the standard deviation of the mean.
Figure 12A:
FIG. 12A–FIG. 12D is a composite photograph of leaves of RGluc-accumulating plants and the control alfalfa after wound-inoculation with the alfalfa fungal pathogen *Phoma medicaginis* showing the development of fungal necrotic lesions and reproductive structures (pycnidia).
Figure 12B:

Two independent alfalfa lines that consistently accumulate the highest levels of RGluc and two independent pGA482 vector control lines were tested for resistance to *P. medicaginis*. First (L1) and second trifoliate (L2) leaves (FIG. 7) were wound-inoculated with small gauge needles that were dipped in spore suspensions varying from $10^4$ to $10^7$ colony forming units (CFU/ml). After ten days, the brown necrotic zone surrounding the wound site was measured. Results in FIG. 10 and FIG. 11 show that over the range of CFU's tested, the area (mm$^2$) of tissue necrosis is reduced on average by as much as 50% as compared to the vector control plants. In addition, the observed area of chlorosis surrounding the necrotic zone also appeared to be greatly reduced. (FIG. 12A and FIG. 12B).

Figure 12C:
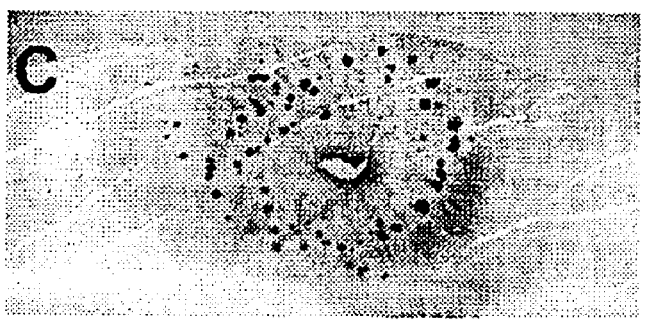
Figure 12D:
Figure 13A:
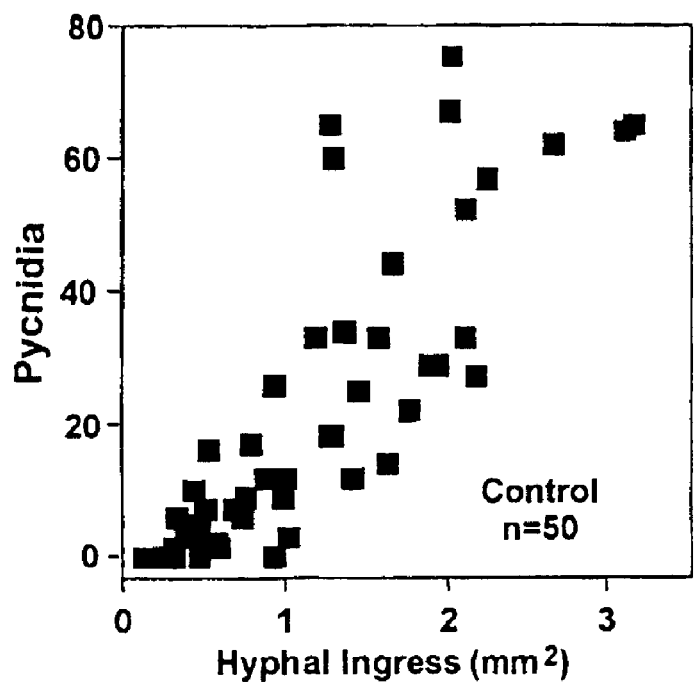
FIGS. 13A and 13B are graphs comparing the extent of hyphal ingress to the number of pycnidia in control alfalfa leaves (FIG. 13A) and RGluc CaMV5S:RS-transformed leaves (FIG. 13B). Following trypan blue staining, the total area of hyphal growth was measured and the number of pycnidia scored in inoculated leaves (CFU/ml=10,000) from the control and CaMV35S:RS lines. For this experiment, the number of lesions measured for control and CaMV35S:RS were n=50 and n=57, respectively.
Figure 13B:
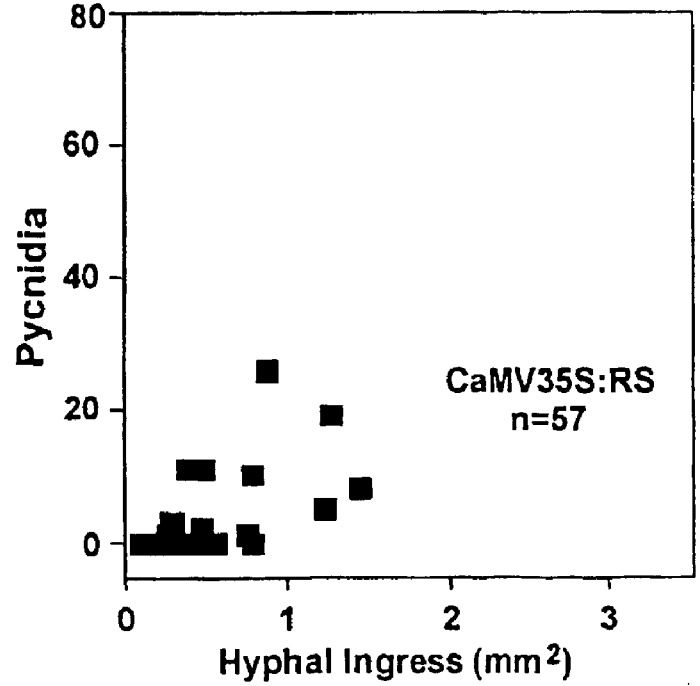

Further evidence of increased resistance to *P. medicaginis* was found after the detached leaves that appeared to be the most resistant ($10^4$ CFU/ml; FIG. 10 and FIG. 11) were allowed to incubate at 100% a relative humidity. After three days, the leaves were stained with trypan blue in order to visualize the extent of hyphal ingress. Results in FIG. 12C show extensive hyphal growth in the vector control line and the formation of reproductive structures (pycnidia). In contrast, only a small area of fungal hyphae (blue staining) outside of the necrotic zone could be observed in inoculated leaves from a CaMV35S:RS trinsgenic line (FIG. 12D). Subsequently, the extent of hyphal ingress outside of the necrotic zone surrounding the wound site and the number of pycnidia were measured. Results in FIG. 13 show the extent of hyphal ingress and number of pycnidia formed beyond the necrotic zone is much greater in the vector control lines than in the CaMV35S:RS lines. In only seven out of fifty-seven lesions examined from the CaMV35S:RS lines could pycnidia be identified, compared to forty-seven out of fifty lesions from the vector controls. Together these experiments demonstrate that the accumulation of RGluc is sufficient to reduce the extent of leaf necrosis, prevent chlorosis caused by hyphal ingress and reduce the number of reproductive structures.

EXAMPLE 2

*Agrobactenum*-mediated Transformation of Soybean

In soybean, the CaMV-35S:RS binary construct or the pGA482 binary vector control plasmid was introduced into

*Agrobacterium rhizogenes* Strain K599 (Savka, et al. 1990. *Phytopathology* 80:503–508) using a standard freeze-thaw technique. *A. rhizogenes* colonies containing the binary vector were selected on YMB agar plates with kanamycin (25 mg/l) and tetracycline (12 mg/l). The composition of the YMB agar plates per liter was 0.45 grams anhydrous dibasic potassium phosphate, 0.2 grams magnesium sulfate (7H$_2$O), 0.1 g sodium chloride, 10 g mannitol, and 0.4 g yeast extract. Components were dissolved in distilled water, the pH adjusted to 6.5, 15 g of bacteriological grade agar (Bactoagar, Gibco, Rockville, Md.) was added, and the mixture was sterilized by autoclaving for thirty minutes at 121° C. After cooling to approximately 50° C., the appropriate antibiotics were added and poured into sterile plastic petri plates. Selected colonies were re-streaked onto fresh plates and used for inoculum.

Soybean seeds (*Glycine max* cv. Harosoy 63) were surface sterilized with 70% ethanol for ten minutes and 20% bleach at a final concentration of approximately 1% sodium hypochlorites for twenty minutes, and then rinsed three times with sterile distilled water. Surface sterilized seeds were then placed on sugar-water-agar (SWA) plates for germination at 23–25° C. with 16 hour light/8 hour dark, with cool-white fluorescent bulbs providing illumination. SWA contains 0.8% Gibco tissue culture grade Phytagar, 0.5% sucrose in distilled water which was autoclaved for 30 minutes, cooled to 50° C., and then poured into 150 mm by 25 mm transparent plastic Petri dishes or pre-sterilized Magenta boxes.).

The cotyledons of nine to eleven-day-old soybean seedlings were wounded using a sharp scalpel dipped into the *Agrobacterium rhizogenes* mass growing on the surface of the YMB plates described above. The seedlings were transferred to transparent plastic Magenta boxes (Magenta Corp, USA, Chicago, Ill.) containing SWA medium, with roots embedded in the medium to hold the seedlings upright. The first morphogenic change, detected at 5–10 days after inoculation, was callus formation at the inoculation sites. Within two weeks, the first roots were visible; they grew directly out of the callus. The number of roots produced varied from four to nine per inoculated cotyledon after 3 weeks. Plants wounded with a sterile scalpel (uninoculated control) did not form roots at the wound site.

Approximately 50 to 60% of the emerging hairy roots were "co-transformed" (contain both the Ri DNA from the genome of the *A. rhizogenes* and the T-DNA region of the introduced binary vector). Individual hairy roots were transferred to Schenk & Hildebranbt (SH) agar medium supplemented with phytohormones (Oommen et al. 1994. *Plant Cell* 6:1789–1803) and carbenicillin (500 mg/ml) to initiate callus from the roots and to eliminate any *A. rhizogenes*. The hairy roots and newly initiated calli were transferred to fresh medium at weekly intervals.

Four to five weeks after initiation, calli were aseptically sampled (100 mg) and analyzed for the presence of the NPT II gene using an NPT II ELISA kit (5Prime3Prime Inc., Boulder, Colo.). Calli induced by *A. rhizogenes* with no binary vector were negative for NPT II ELISA. Calli positive by this ELISA assay contained at least part of the T-DNA region from the binary vector. After further increases in the calli mass, these positive calli (and representative non-transformed calli) were then assayed for the presence of RGluc and the presence of the CaMV-35S:RS construct, using the techniques similar to those used for the transgenic alfalfa. From each pGA482 vector control and CaMV-35S:RS transgenic callus line, approximately 25 grams of soybean callus cells were aseptically removed from the culture dish, and submerged in 150 ml acetone to extract the phenolic compounds. After two days shaking, the mixture was centrifuged, the acetone extract taken to dryness on a rotary evaporator unit, and the residue dissolved in methanol. After centrifugation, this extract was analyzed by HPLC, as described for the alfalfa extracts.

Figure 14:
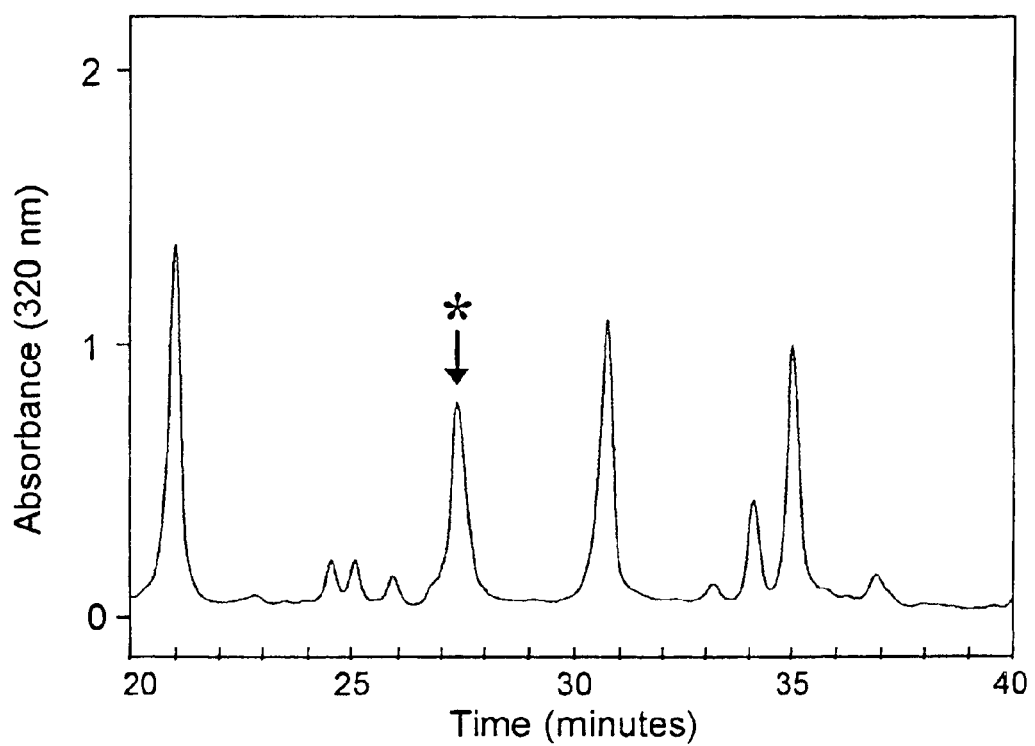
FIG. 14 is a HPLC chromatogram of an extract from a transgenic soy callus transformed with the construct described in FIG. 2. The RGluc peak is marked by "★".
Figure 15:
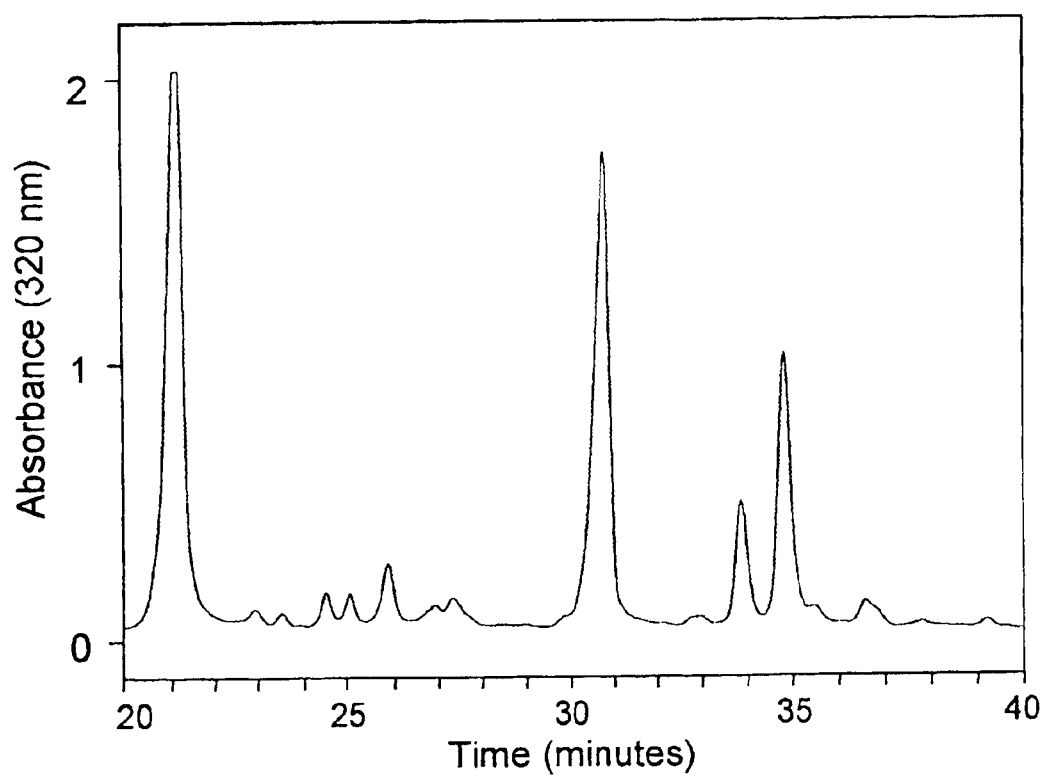
FIG. 15 is a HPLC chromatogram of an extract from a non-transgenic soy callus.
Figure 16:
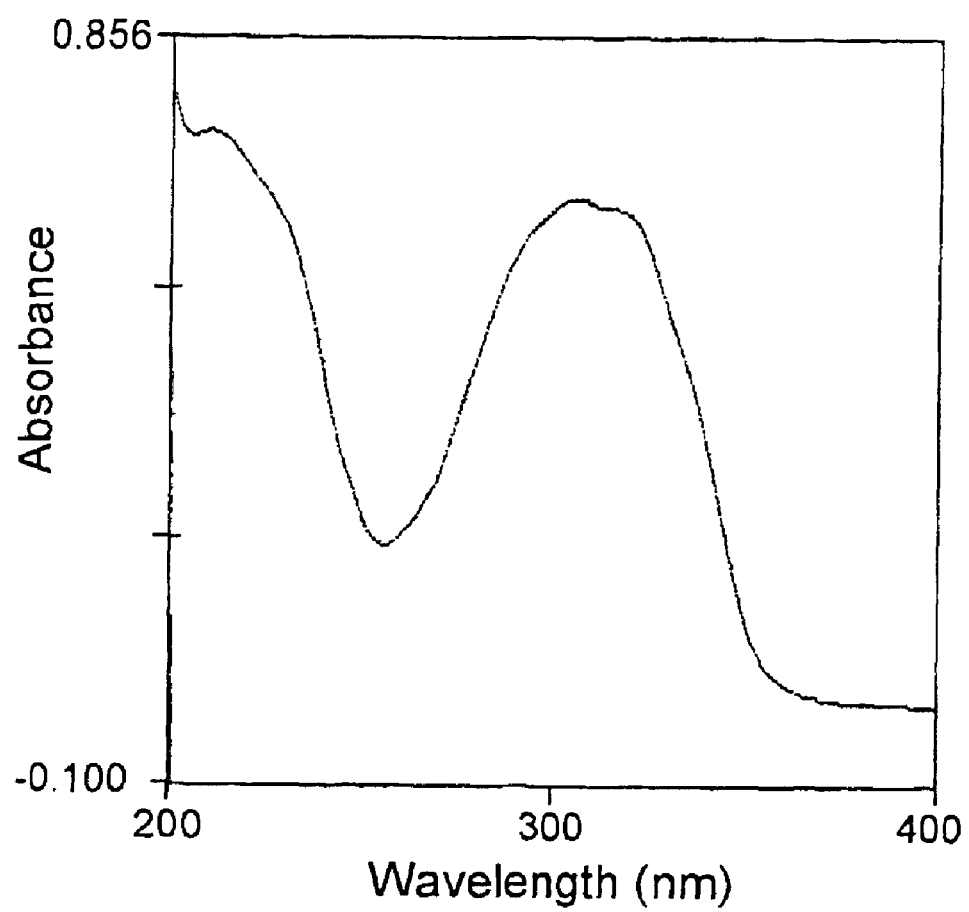
FIG. 16 is the ultra-violet diode array scan of the soybean callus-generated RGluc peak.
Figure 17:
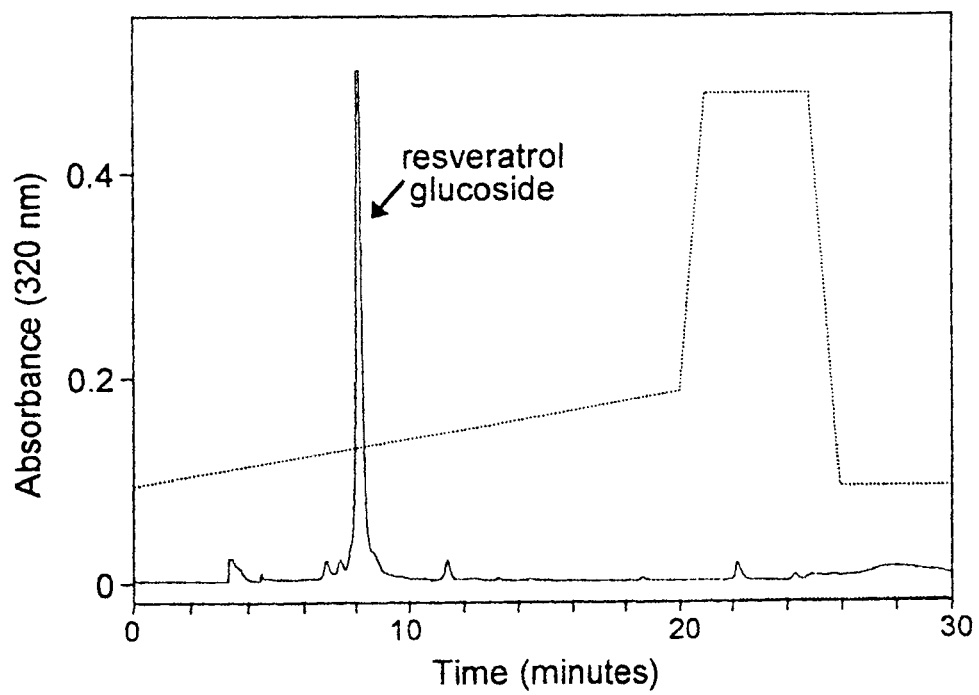
FIG. 17 is a HPLC chromatogram which demonstrates RGluc partially purified from transgenic soybean callus before treatment with beta-glucosidase.
Figure 18:
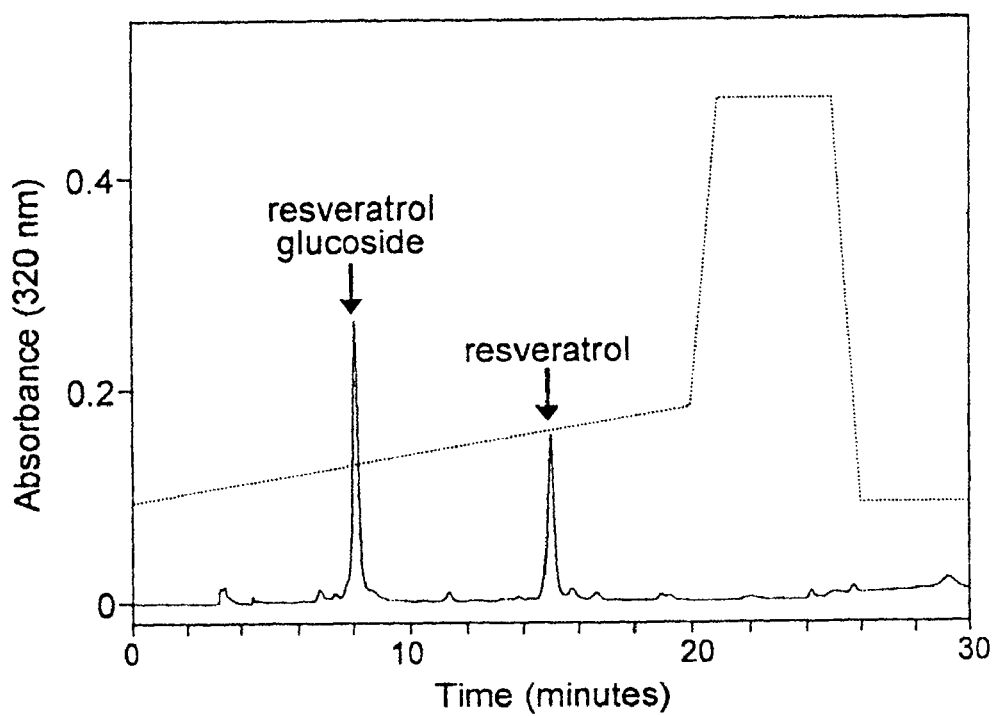
FIG. 18 is a HPLC chromatogram which demonstrates partially purified RGluc after brief treatment with beta-glucosidase.

Stilbenes have not been reported to accumulate in soybean plants, seeds, cell cultures or food products. No RGluc was observed in the control (nontransformed soybean callus extracts). A new peak was present in the HPLC chromatograms for CaMV-3S:RS transformed calli. This new compound was identified as RGluc, based on the observation that its properties were identical to the RGluc from alfalfa (identical HPLC retention time, lack of change in retention time which mobile phase component is changed from 1% H$_3$PO$_4$ to pure H$_2$O, identical UV diode array scan, UV scan similar to free resveratrol, ability to be hydrolyzed to free resveratrol by beta-glucosidase, etc.)(FIG. 14). FIG. 14 shows the HPLC chromatogram of a transgenic soy callus with a RGluc peak at 27 minutes. FIG. 15 shows the HPLC chromatogram of a non-transgenic soy callus line. To enhance the resolution of the RGluc from the endogenous soybean cell phenolics in crude extracts as in FIG. 14, the gradient was altered from that used for alfalfa plants extracts. The gradient for crude soy extracts was 90% water/10% CH$_3$CN initially with a linear change to 25% CH$_3$CN in 45 minutes. FIG. 16 is the UV diode array scan of the soybean callus-generated RGluc peak, which matches closely the alfalfa-generated peak (FIG. 5). FIG. 17 shows the RGluc partially purified from soy callus before treatment with 1 mg beta-glucosidase, and FIG. 18 shows the RGluc partially purified from soy callus after treatment with 1 mg beta-glucosidase (from almonds; Sigma, St. Louis) for 45 minutes in pH5.5 citrate/phosphate buffer. Samples in FIG. 17 and FIG. 18 were generated using the same extraction, purification, and HPLC analytical methods as were used for the transgenic RGluc alfalfa studies. RGluc was eluted at approximately 8 minutes and the resveratrol was eluted at approximately 15 minutes.

These transgenic plant cell callus cultures, or those of a similarly transformed species, can be grown axenically for years as callus or as cell suspension cultures to produce large quantities of RGluc-containing cells for direct use, or for the production of extracts containing RGluc, or for the production of purified RGluc.

EXAMPLE 3

RGluc-produciug Transgenic Alfalfa Diet for Mouse

Because alfalfa is a highly nutritious animal feed, a study was carried out to compare the chemopreventative activity of a basal diet and a diet supplement with dried transgenic RGluc accumulating alfalfa.

The transgenic alfalfa was dried for 24–48 hours in a convection oven, powdered in a cyclone grinding mill to a particle size of less than one millimeter, and then blended at a rate of 20% weight/weight into the basic diet, which was then formed into food pellets. Four replicate samples of the dried powdered alfalfa was extracted with 90% acetone/10% water for a 24 hour period. The extract was taken to dryness and resuspended in methanol and subjected to HPLC analysis for RGluc. The powdered alfalfa contained 162 micrograms RGluc (equivalent on a molar basis to approximately 95 micrograms resveratrol).

The assay used was the mouse aberrant crypt foci (ACF) system (Olivo, S. and Wargovich, M. J. 1998. "Inhibition of aberrant crypt foci by chemopreventive agents," *Vivo-Attiki* 12:159–166). Mice were injected with varying levels of tumor-inducing compound azoxymethane (AOM; 10 mg/kg body weight weekly) for five weeks while being fed basal diet, the mice were then fed test diets for five weeks, and the number of putative precancerous lesions in the colon (ACF) in the colon were subsequently recorded. Mice in the group receiving the RGluc-alfalfa supplemented diet consumed approximately 4.8±0.2 grams per day, which indicates an average dose of 155 micrograms of RGluc per day (or 91 micrograms resveratrol per day), which translates to approximately 4.7 mg RGluc per kg body weight ( or 2.8 mg resveratrol per kg body weight). Preliminary experiments indicate that supplementation of the basal diet with 10 and 20% (weight/weight) powdered alfalfa did not significantly affect the body weight or food consumption, indicating that the diets were well matched in nutritional qualities and caloric content.

Mice receiving the control diet achieved an average body weight of 31.3 g ±1.3 g and were found to have an average of 30.8±10.2 foci/colon. Mice receiving the RGluc-alfalfa supplemented diet achieved an average body weight of 32.8±2.2 g and were found to have an average of 21.6±5.5 foci/colon. Compared to ACF numbers in mice fed a basal (control) diet, a significant reduction in ACF number was noted when mice were fed a diet supplement with dried transgenic RGluc accumulating alfalfa. These results indicate that the a diet supplemented with dried transgenic RGluc accumulating alfalfa inhibited colon carcinogenesis in mammals.

It is to be understood that the above description is of preferred exemplary embodiments of the invention and is intended to be illustrative of the invention, but is not to be construed to limit the scope of the invention in any way. Modifications may be made in the structural features of the invention without departing from the scope of the invention. It will be readily apparent to those skilled in the art that alternative materials may also be utilized without departing from the scope of the invention.

We claim:

1. Edible plant material comprising transgenic legume plant cells transformed with a resveratrol synthase transgene under the control of a constitutive promoter whereby said transgenic legume plant cells accumulate resveratrol glucoside upon expression of said resveratrol synthase transgene, wherein said edible plant material exhibits an increased concentration of resveratol glucoside as compared to edible plant material consisting of non-transgenic plant cells of the same cell type grown under the same conditions.

2. The edible plant material of claim 1, wherein said edible plant material is suitable for consumption as a food stuff, a nutritional supplement, an animal feed supplement, or a nutraceutical in the form of a live or harvested whole plant or plant part.

3. The edible plant material of claim 1, wherein said resveratrol synthase transgene encodes the amino acid sequence of SEQ ID NO:2.

4. The edible plant material of claim 2, wherein said resveratrol synthase transgene encodes the amino acid sequence of SEQ ID NO:2.

5. The edible plant material of claim 1, wherein said plant is alfalfa.

6. The edible plant material of claim 1, wherein said plant is soybean.

7. A composition comprising edible plant material, said edible plant material comprising transgenic legume plant cells transformed with a resveratrol synthase transgene under the control of a constitutive promoter whereby said transgenic legume plant cells accumulate resveratrol glucoside upon expression of said resveratrol synthase transgene, wherein the percentage of resveratrol glucoside in said composition obtained by adding a given weight of said edible plant material comprising said transgenic legume plant cells to said composition is higher than the percentage of resveratrol glucoside obtainable by adding instead the same weight of edible plant material consisting of non-transgenic plant cells of the same cell type grown under the same conditions to said composition.

8. The composition of claim 7, wherein said composition is suitable for consumption as a food stuff, a nutritional supplement, an animal feed supplement, or a nutraceutical.

9. The composition of claim 7, wherein said resveratrol synthase transgene encodes the amino acid sequence of SEQ ID NO:2.

10. The composition of claim 8, wherein said resveratrol synthase transgene encodes the amino acid sequence of SEQ ID NO:2.

11. The composition of claim 7, wherein said legume plant is alfalfa.

12. The composition of claim 7, wherein said legume plant is soybean.

13. An edible legume plant comprising transgenic legume plant cells transformed with a resveratrol synthase transgene under the control of a constitutive promoter whereby said transgenic legume plant cells accumulate resveratrol glucoside upon expression of said resveratrol synthase transgene, wherein said edible legume plant exhibits an increased concentration of resveratrol glucoside as compared to an edible legume plant comprising non-transgenic plant cells of the same cell type grown under the same conditions.

14. The edible legume plant of claim 13, wherein said edible plant is suitable for consumption as a food stuff, a nutritional supplement, an animal feed supplement, or a nutraceutical in the form of a live or harvested whole plant or a plant part.

15. The edible legume plant of claim 13, wherein said resveratrol synthase transgene encodes the amino acid sequence of SEQ ID NO:2.

16. The edible legume plant of claim 14, wherein said resveratrol synthase transgene encodes the amino acid sequence of SEQ ID NO:2.

17. The edible legume plant of claim 13, wherein said plant is alfalfa.

18. The edible legume plant of claim 13, wherein said plant is soybean.

19. Seed from the edible legume plant of claim 13, 14, 15, or 16 which comprises said resveratrol synthase transgene.

20. Progeny from the edible legume plant of claim 13, 14, 15 or 16 which comprises said resveratrol synthase transgene.

21. Progeny from the seed of claim 19 which comprises said resveratrol synthase transgene.

22. A method of using an edible legume plant comprising transforming plant cells of said edible legume plant with a resveratrol synthase transgene under the control of a constitutive promoter to form transgenic plant cells whereby said transgenic plant cells accumulate resveratrol glucoside upon expression of said resveratrol synthase transgene, wherein said edible legume plant exhibits an increased concentration of resveratrol glucoside as compared to an edible legume plant comprising non-transgenic plant cells of the same cell type grown under the same conditions and consuming said edible legume plant to provide a nutraceutical benefit to a human or animal.

23. The method of claim 22, wherein said transgene encodes the amino acid sequence of SEQ ID NO:2.

24. A method of increasing disease resistance in an edible legume plant comprising transforming cells of said plant with a resveratrol synthase transgene under the control of a constitutive promoter whereby said transgenic plant cells accumulate resveratrol glucoside upon expression of said resveratrol synthase transgene, wherein said edible legume plant exhibits an increased concentration of resveratrol glucoside as compared to an edible legume plant comprising non-transgenic plant cells of the same cell type grown under the same conditions.

25. The method of claim 24, wherein said transgene encodes the amino acid sequence of SEQ ID NO:2.

26. Seed from the edible legume plant of claim 17 which comprises said resveratrol synthase transgene.

27. Seed from the edible legume plant of claim 18 which comprises said resveratrol synthase transgene.

28. Progeny from the edible legume plant of claim 17 which comprises said resveratrol synthase transgene.

29. Progeny from the edible legume plant of claim 18, which comprises said resveratrol synthase transgene.

30. Progeny from the seed of claim 26 which comprises said resveratrol synthase transgene.

31. Progeny from the seed of claim 27 which comprises said resveratrol synthase transgene.

32. The edible plant of claim 13, wherein said edible legume plant is useful as a source for isolated resveratrol glucoside.

* * * * *